(12) United States Patent
Valenta et al.

(10) Patent No.: US 7,482,009 B2
(45) Date of Patent: Jan. 27, 2009

(54) NON-ANAPHYLACTIC FORMS OF GRASS POLLEN PHL P 6 ALLERGEN AND THEIR USE

(75) Inventors: Rudolf Valenta, Theresienfeld (AT); Susanne Vrtala, Vienna (AT); Sabine Stummfoll, St. Peter (AT); Hans Grönlund, Lidingö (SE); Monika Grote, Münster (DE); Luca Vangelista, Padua (IT); Annalisa Pastore, London (GB); Wolfgang R. Sperr, Vienna (AT); Peter Valent, Vienna (AT); Dietrich Kraft, Vienna (AT)

(73) Assignee: Phadia AB, Uppsala (SE)

( * ) Notice: Subject to any disclaimer, the term of this patent is extended or adjusted under 35 U.S.C. 154(b) by 46 days.

(21) Appl. No.: 10/142,049

(22) Filed: May 10, 2002

(65) Prior Publication Data

US 2003/0077290 A1    Apr. 24, 2003

Related U.S. Application Data

(62) Division of application No. 09/696,169, filed on Oct. 26, 2000, now Pat. No. 6,572,859.

(60) Provisional application No. 60/164,148, filed on Nov. 8, 1999.

(30) Foreign Application Priority Data

Oct. 29, 1999    (SE)    .................... 9903950

(51) Int. Cl.
  A61K 39/00    (2006.01)
  A61K 39/35    (2006.01)
  A61K 39/36    (2006.01)
  A61K 38/00    (2006.01)
  A01N 37/18    (2006.01)

(52) U.S. Cl. .............. 424/185.1; 424/185.1; 424/275.1; 514/2

(58) Field of Classification Search .............. 424/185.1, 424/275.1; 530/379
See application file for complete search history.

(56) References Cited

U.S. PATENT DOCUMENTS 5,026,545 A * 6/1991 Saint-Remy et al. ..... 424/146.1

FOREIGN PATENT DOCUMENTS

| WO | WO9843657 | 10/1998 |
| WO | WO9916467 | 4/1999 |
| WO | WO 99/34826 | * 7/1999 |
| WO | WO9934826 | 7/1999 |

OTHER PUBLICATIONS

Petersen et al, Int Arch Allergy Immunol 108: 49-54; 1995.*
Mohapatra et al, Allergy 50(25): 37-44; 1995.*
Schramm et al, J Immunol 162: 2406-2414, Feb. 1999.*
Larche et al., Allergens and Allergen Immnotherapy, 3rd edition, 2004, pp. 648-649.*
Fathman et al. 'Molecular mechanisms of CD4+ T-cell anergy.' Nature Reviews 7:599-609, 2007.*
Petersen et al., *Int. Arch. Allergy. Immunol.*, vol. 108 (1995) pp. 55-59.
G. Schramm et al., *J. Immunol.*, vol. 162, No. 4 (1999) pp. 2406-2414.
S. Vrtala et al., *J. Immunol.*, vol. 163 (1999) pp. 5489-5496.
P. Norman, *Advances in Medicine*, vol. 41 (1996) pp. 681-713.
S. Vrtala et al., *J. Clin. Invest.*, vol. 99, No. 7 (1997) pp. 1673-1681.
S. Schenk et al., *J. Allergy Clin. Immunol.*, vol. 96, No. 6 (1995) pp. 986-996.
R.J. Joost van Neervan et al., *J. Immunol.*, vol. 151, No. 4 (1993) pp. 2326-2335.
C. Ebner et al., *J. Immunol.*, vol. 150, No. 3 (1993) pp. 1047-1054.
P. S. Norman, *Cur. Opinion in Immunol.*, vol. 5 (1993) pp. 968-973.
T. J. Briner et al., *Proc. Natl. Acad. Sci.*, vol. 90 (1993) pp. 7608-7612.
Petersen et al., *Int. Arch. Allergy Immunol.* vol. 108: pp. 49-54, (1995).
Mohapatra et al., *Allergy* 50(25), pp. 37-44, (1995).

* cited by examiner

*Primary Examiner*—Maher M Haddad
*Assistant Examiner*—Nora M Rooney
(74) *Attorney, Agent, or Firm*—Porter, Wright, Morris & Arthur LLP

(57) ABSTRACT

The invention relates to a hypoallergenic immunogenic molecule derived from the Phl p 6 allergen, wherein the Phl p6 molecule has an N-terminal and/or C-terminal deletion which makes the molecule at least substantially lack IgE binding capacity. The invention also relates to a hypoallergenic immunogenic combination of molecules derived from the Phl p 6 allergen, comprising (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete sequence of Phl p 6. The invention further relates to the use of the hypoallergenic immunogenic molecule or molecule mixture in hyposensitization and diagnosis.

7 Claims, 11 Drawing Sheets

SEQUENCE LISTING

```
<160> NUMBER OF SEQ ID NOS: 21

<210> SEQ ID NO 1
<211> LENGTH: 29
<212> TYPE: DNA
<213> ORGANISM: Artificial Sequence
<220> FEATURE:
<223> OTHER INFORMATION: Primer derived from Phleum pratense

<400> SEQUENCE: 1
gggaattcca tatggggaag gccacgacc                                    29

<210> SEQ ID NO 2
<211> LENGTH: 45
<212> TYPE: DNA
<213> ORGANISM: Artificial Sequence
<220> FEATURE:
<223> OTHER INFORMATION: Primer derived from Phleum pratense

<400> SEQUENCE: 2
cggggtaccc tagtggtggt ggtggtggtg gggcgccttt gaaac                  45

<210> SEQ ID NO 3
<211> LENGTH: 29
<212> TYPE: DNA
<213> ORGANISM: Artificial Sequence
<220> FEATURE:
<223> OTHER INFORMATION: Primer derived from Phleum pratense

<400> SEQUENCE: 3
```
gggaattcca tatggcagac aagtataag                                    29

<210> SEQ ID NO 4
<211> LENGTH: 45
<212> TYPE: DNA
<213> ORGANISM: Artificial Sequence
<220> FEATURE:
<223> OTHER INFORMATION: Primer derived from Phleum pratense

<400> SEQUENCE: 4
ccggaattcc tagtggtggt ggtggtggtg cgcgccgggc ttgac                  45

<210> SEQ ID NO 5
<211> LENGTH: 4
<212> TYPE: PRT
<213> ORGANISM: Phleum pratense

<400> SEQUENCE: 5

Gly Lys Ala Thr
1

<210> SEQ ID NO 6
<211> LENGTH: 4
<212> TYPE: PRT
<213> ORGANISM: Phleum pratense

<400> SEQUENCE: 6

Lys Ala Thr Thr
1

<210> SEQ ID NO 7
<211> LENGTH: 4
<212> TYPE: PRT
<213> ORGANISM: Phleum pratense

<400> SEQUENCE: 7

Lys Tyr Lys Thr
1

<210> SEQ ID NO 8
<211> LENGTH: 138
<212> TYPE: PRT
<213> ORGANISM: Phleum pratense

<400> SEQUENCE: 8

Met Ala Ala His Lys Phe Met Val Ala Met Phe Leu Ala Val Ala Val
1               5                   10                  15

Val Leu Gly Leu Ala Thr Ser Pro Thr Ala Glu Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu Arg Ile Ile Ala Gly Thr
        115                 120                 125

```
Pro Glu Val His Ala Val Lys Pro Gly Ala
    130                 135
```

<210> SEQ ID NO 9
<211> LENGTH: 750
<212> TYPE: DNA
<213> ORGANISM: Phleum pratense

<400> SEQUENCE: 9

| | | | | | |
|---|---|---|---|---|---|
| ctatccctcc | tacaaaccaa | cgcacgagta | gcaatggcag | cgcacaagtt | catggtggcg | 60 |
| atgttcctcg | ctgttgccgt | tgtgttgggc | ttggccacat | ccccaactgc | agagggaggg | 120 |
| aaggccacga | ccgaggagca | aaaattgatc | gaggacatca | atgccagctt | tagggcggcc | 180 |
| atggccacca | ctgctaacgt | ccctccagca | gacaagtata | agacattcga | agccgccttc | 240 |
| acggtgtcct | caaagagaaa | cctcgctgac | gccgtttcaa | aggcgcccca | gctggtcccc | 300 |
| aagctcgatg | aagtctacaa | cgccgcctac | aatgctgccg | atcatgccgc | ccagaagac | 360 |
| aagtatgaag | ccttcgtcct | tcacttttcc | gaggctctcc | acatcatcgc | cggtaccccc | 420 |
| gaggtccacg | ctgtcaagcc | cggcgcgtag | ttgttcagca | cggtcaagat | ccttgacagc | 480 |
| gtcgctgcca | ccggcgctgc | agccaacact | gccagtggct | aaaaaattcg | actagctcct | 540 |
| tcatacaatg | aatacacatg | tatcattcaa | acatactact | gtacagtatg | tgcatgacct | 600 |
| agcggcgagc | atttttttta | tgattaatct | tttatacatg | ggcgtgatcg | agcgtgtgca | 660 |
| tatgtgtaat | aattaatttt | ttattttgat | ttgaaattgt | aatcctgata | agaaatgcga | 720 |
| ttaagtccat | ttatgaaaaa | aaaaaaaaaa | | | | 750 |

<210> SEQ ID NO 10
<211> LENGTH: 571
<212> TYPE: DNA
<213> ORGANISM: Phleum pratense

<400> SEQUENCE: 10

| | | | | | |
|---|---|---|---|---|---|
| ccaacgcacg | agtagcaatg | gcagcgcaca | agttcatggt | ggcgatgttc | ctcgctgttg | 60 |
| ccgttgtgtt | gggcttggcc | acatccccaa | ctgcagaggg | agggaaggcc | acgaccgagg | 120 |
| agcaaaaatt | gattgaggac | gtcaatgcca | gctttagggc | ggccatggcc | accactgcta | 180 |
| acgtccctcc | agcagacaag | tataagacat | tcgaagccgc | cttcacggtg | tcctcaaaga | 240 |
| gaaacctcgc | tgacgccgtt | tcaaaggcgc | cccagctggt | ccccaagctc | gatgaagtct | 300 |
| acaacgccgc | ctacaatgct | gccgatcatg | ccgcccagaa | agacaagtat | gaagccttcg | 360 |
| tccttcactt | ttccgaggct | ctccgtatca | tcgccggtac | ccccgaggtt | cacgctgtca | 420 |
| agcccggcgc | gtagttgttc | agcacggtca | agatccttga | cagcgtcgct | gccaccggcg | 480 |
| ctgcagccaa | cactgccagt | ggctaaaaaa | ttcgactagc | tccttcatac | aatgaataca | 540 |
| catgtatcat | tcaaaaaaaa | aaaaaaaaaa | a | | | 571 |

<210> SEQ ID NO 11
<211> LENGTH: 647
<212> TYPE: DNA
<213> ORGANISM: Phleum pratense

<400> SEQUENCE: 11

| | | | | | |
|---|---|---|---|---|---|
| accgaggagc | aaaaattgat | cgaggacgtc | aatgccagct | ttagggcggc | catggccacc | 60 |
| actgctaacg | tccctccagc | agacaagtat | aagacattag | aagccgcctt | cacggtgtcc | 120 |
| tcaaagagaa | acctcgctga | cgccgtctca | aaggcgcccc | agctcgtccc | caagctcgat | 180 |

```
gaagtctaca acgccgccta caatgctgcc gatcatgccg ccccagaaga caagtatgaa    240
gccttcgtcc ttcactttc cgaggctctc cgtatcatcg ccggtacccc cgaggtccac    300
gctgtcaagc ccggcgcgta gttgttcagc acggtcaaga tccttgacag cgtcgctgcc    360
accggtgctg cagccaacac tgccagtggc taaaaagttc gaccagctct tcatacaat    420 gaatacacat gtatctttca aacatactac tgtacagtat gtgcatgacc tagcggcgag    480 cattttttt atgattaatc ttttatacat gggcgtgatc gagcgtgtgc atatgtgtaa    540
taattaattt cttattttga tttgaaattg taatcctgat aagaaatgcg attaagtcca    600
tttatgaaat atagatggtc cgtcgttatt taaaaaaaaa aaaaaa                 647

<210> SEQ ID NO 12
<211> LENGTH: 572
<212> TYPE: DNA
<213> ORGANISM: Phleum pratense

<400> SEQUENCE: 12
gcagacaagt ataagacatt cgaagccgcc ttcacggtgt cctcaaagag aaacctcgct    60
gacgccgttt caaaggcgcc ccagctggtc cccaagctcg atgaagtcta caacgccgcc    120
tacaatgctg ccgatcatgc cgccccagaa gacaagtatg aagccttcgt ccttcacttt    180
tccgaggctc tccacatcat cgccggtacc cccgaggtcc acgctgtcaa gcccggcgcg    240
tagttgttca gcacggtcaa gatccttgac agcgtcgctg ccaccggcgc tgcagccaac    300
actgccagtg gctaaaaaat tcgactagct ccttcataca atgaatacac atgtatcatt    360
caaacatact actgtacagt atgtgcatga cctagcggcg agcattttt ttatgattaa    420 tcttttatac atgggcgtga tcgagcgtgt gcatatgtgt aataattaat ttttatttt    480 gatttgaaat tgtaatcctg ataagaaatg cgattaagtc catttaaaaa aaaaaaaaa    540 aaaaaaaaaa aaaaaaaaaa aa                                           572

<210> SEQ ID NO 13
<211> LENGTH: 474
<212> TYPE: DNA
<213> ORGANISM: Phleum pratense

<400> SEQUENCE: 13
tcaaaggcgc cccagctggt ccccaagctc gatgaagtct acaacgccgc ctacaatgct    60
gccgatcatg ccgccccaga agacaagtat gaagccttcg tccttcactt ttccgaggct    120
ctccacatca tcgccggtac ccccgaggtc cacgctgtca agcccggcgc gtagttgttc    180
agcacggtca gatccttga cagcgtcgct gccaccggcg ctgcagccaa cactgccagt    240
ggctaaaaaa ttcgactagc tccttcatac aatgaataca catgtatcat tcaaacatac    300
tactgtacag tatgtgcatg acctagcggc gagcattttt tttatgatta atctttata    360 catgggcgtg atcgagcgtg tgcatatgtg taataattaa tttttttatt tgatttgaaa    420
ttgtaatcct gataagaaat gcgattaagt ccatttatga aaaaaaaaaa aaaa        474

<210> SEQ ID NO 14
<211> LENGTH: 554
<212> TYPE: DNA
<213> ORGANISM: Phleum pratense

<400> SEQUENCE: 14
cagctggtcc ccaagctcga tgaagtctac aacgccgcct acaatgctgc cgatcatgcc    60
```

```
gccccagaag acaagtatga agccttcgtc cttcactttt ccgaggctct ccacatcatc    120
gccggtaccc ccgaggtcca cgctgtcaag cccggcgcgt agttgttcag cacggtcaag    180
atccttgaca cgtcgctgc caccggcgct gcagccaaca ctgccagtgg ctaaaaaatt     240
cgactagctc cttcatacaa tgaatacaca tgtatcattc aaacatacta ctgtacagta    300
tgtgcatgac ctagcggcga gcattttttt tatgattaat cttttataca tgggcgtgat    360
cgagcgtgtg catatgtgta ataattaatt ttttattttg atttgaaatt gtaatcctga    420
taagaaatgc gattaagtcc atttatgaaa tatagatggt ctgtcgttat ttaaaaaaaa    480
aaaaaaaaaa aaaaaaaaaa aaaaaaaaaa aaaaaaaaaa aaaaaaaaaa aaaaaaaaaa    540
aaaaaaaaaa aaaa                                                      554
```

<210> SEQ ID NO 15
<211> LENGTH: 138
<212> TYPE: PRT
<213> ORGANISM: Phleum pratense

<400> SEQUENCE: 15

```
Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu His Ile Ile Ala Gly Thr
        115                 120                 125

Pro Glu Val His Ala Val Lys Pro Gly Ala
    130                 135
```

<210> SEQ ID NO 16
<211> LENGTH: 138
<212> TYPE: PRT
<213> ORGANISM: Phleum pratense

<400> SEQUENCE: 16

```
Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95
```

Ala Ala Tyr Asn Ala Ala Asp His Ala Ala Pro Glu Asp Lys Tyr Glu
                100                 105                 110

Ala Phe Val Leu His Phe Ser Glu Ala Leu Arg Ile Ile Ala Gly Thr
            115                 120                 125

Pro Glu Val His Ala Val Lys Pro Gly Ala
        130                 135

<210> SEQ ID NO 17
<211> LENGTH: 106
<212> TYPE: PRT
<213> ORGANISM: Phleum pratense

<400> SEQUENCE: 17

Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
            20                  25                  30

Leu Glu Ala Ala Phe Thr Val Ser Ser Lys Arg Asn Leu Ala Asp Ala
        35                  40                  45

Val Ser Lys Ala Pro Gln Leu Val Pro Lys Leu Asp Glu Val Tyr Asn
50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
            100                 105

<210> SEQ ID NO 18
<211> LENGTH: 80
<212> TYPE: PRT
<213> ORGANISM: Phleum pratense

<400> SEQUENCE: 18

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

His Ile Ile Ala Gly Thr Pro Glu Val His Ala Val Lys Pro Gly Ala
65                  70                  75                  80

<210> SEQ ID NO 19
<211> LENGTH: 57
<212> TYPE: PRT
<213> ORGANISM: Phleum pratense

<400> SEQUENCE: 19

Ser Lys Ala Pro Gln Leu Val Pro Lys Leu Asp Glu Val Tyr Asn Ala
1               5                   10                  15

Ala Tyr Asn Ala Ala Asp His Ala Ala Pro Glu Asp Lys Tyr Glu Ala
            20                  25                  30

Phe Val Leu His Phe Ser Glu Ala Leu His Ile Ile Ala Gly Thr Pro
        35                  40                  45

Glu Val His Ala Val Lys Pro Gly Ala

-continued

```
<210> SEQ ID NO 20
<211> LENGTH: 53
<212> TYPE: PRT
<213> ORGANISM: Phleum pratense

<400> SEQUENCE: 20

Gln Leu Val Pro Lys Leu Asp Glu Val Tyr Asn Ala Ala Tyr Asn Ala
1               5                   10                  15

Ala Asp His Ala Ala Pro Glu Asp Lys Tyr Glu Ala Phe Val Leu His
            20                  25                  30

Phe Ser Glu Ala Leu His Ile Ile Ala Gly Thr Pro Glu Val His Ala
        35                  40                  45

Val Lys Pro Gly Ala
    50

<210> SEQ ID NO 21
<211> LENGTH: 57
<212> TYPE: PRT
<213> ORGANISM: Phleum pratense

<400> SEQUENCE: 21

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro
    50                  55
```

NON-ANAPHYLACTIC FORMS OF GRASS POLLEN PHL P 6 ALLERGEN AND THEIR USE

This application is a divisional of U.S. application Ser. No. 09/696,169, filed on Oct. 26, 2000, now U.S. Pat. No. 6,572,859, the entire contents of which are hereby incorporated by reference and for which priority is claimed under 35 U.S.C. § 120; and this application claims priority of Application No. 9903950-S filed in Sweden on Oct. 29, 1999 and Application No. 60/164,148 filed in the United States on Nov. 8, 1999 under 35 U.S.C. § 119.

FIELD OF THE INVENTION

The present invention relates to non-anaphylactic, i.e. hypoallergenic, forms of the major timothy grass pollen allergen Phl p 6 and the use of the forms for hyposensitization and for diagnosis. The invention also relates to a method for hyposensitization of a mammalian individual, typically a human individual, suffering from type I allergy against the Phl p 6 allergen.

This application contains a Substitute Sequence Listing located after the abstract. The paper copy of the Substitute Sequence Listing is identical to the computer readable form of the Substitute Sequence Listing except that it lacks formatting.

BACKGROUND OF THE INVENTION

Type I allergy is a genetically determined hypersensitivity disease that affects more than 20% of the population in industrialized countries [Kay, A. B., Allergy and Allergic Diseases, 1997]. As a consequence of this immuno-disorder, allergic patients produce IgE antibodies against per se innocuous, mostly air-born proteins from pollen, mites, moulds and animal hair/dander. The symptoms of Type I allergy (allergic rhinitis, conjunctivitis, allergic asthma and anaphylactic shock) result from allergen-induced crosslinking of effector cell (mast cell, basophil)-bound IgE antibodies and subsequent release of inflammatory mediators [Segal, et al., *PNAS USA* 41:457, 1977]. Since approximately 40% of allergic individuals suffer symptoms following contact with grass pollen, research has concentrated on the characterization of relevant grass pollen allergens by protein and immunochemical methods [Freidhoff et al., *Allergy Clin. Immunol.* 78:1190, 1986]. While groups of major allergens have been identified as cross-reactive moieties that occur in most grass species [Niederberger et al., *J. Allergy Clin. Immunol.* 102:258, 1998], nothing was known concerning their nature and biological functions.

The recent application of molecular biological techniques to allergen characterization has revealed the primary structures of allergens and facilitated the production of recombinant allergens for diagnostic and therapeutic purposes [Valenta et al., *Curr. Opin. Immunol.* 7:751, 1995]. Components of the plant cytoskeleton (e. g., profilin) [Valenta et al., *Science* 253:557, 1991] as well as calcium-binding pollen proteins [Seiberler et al., *EMBO J.* 13:3481, 1994] have been identified as relevant allergens. The fact that allergic patients exhibit immediate type reactions upon contact with various unrelated allergen sources thus can be explained by cross-reactivity of their IgE antibodies with ubiquitous allergens. Evidence that group 1 grass pollen allergens belong to a family of cell wall-loosening proteins (expansins) [Shcherban et al., *PNAS USA* 92:9245, 1995] and grass group 5 allergens may possess RNAse activity [Bufe et al., FEBS Lett. 363:6] has restimulated ideas that the biological function of a given protein may be related to its allergenicity. The recent findings that major grass pollen allergens can either become attached to small sized particles (e. g., group 1 allergens to diesel exhaust [Knox et al., *Clin. Exp. Allergy* 27:246, 1997]) or may become airborne as small pollen subcompartments (e. g., group 5 allergens in amyloplasts [Suphioglu et al., *Lancet* 339:569, 1992]) would provide a possible mechanism of how certain allergens may be able to reach the deep airways of patients and to elicit allergic asthma.

Therapy of Type I allergic diseases is currently performed by pharmacological treatment and by specific immunotherapy. Specific immunotherapy has been established already early in this century (Noon, *Lancet* 1: 1572-1573 (1911)) and involves the systemic application of increasing doses of allergens for extended periods. Although specific immunotherapy is recognized as effective treatment, the occurrence of anaphylactic side effects represents one of the major disadvantages of this therapy. To reduce anaphylactic reactions the use of T-cell epitopes has recently been proposed for allergen specific immunotherapy (Briner et al., *PNAS USA* 90:7608-7612 (1993), and Norman, *Curr. Opin. Immunol.* 5 :986-973 (1993)). Allergens harbour a great variety of different T-cell epitopes (Ebner et al., *J. Immunol* 150:1047-1054 (1993); Joost-van-Neerven et al., *J. Immunol.* 151:2326-2335 (1993); and Schenket al., *J. Allergy Clin. Immunol.* 96:986-996 (1995)) which may overlap with continuous IgE-epitopes. To prevent crosslinking of effector cell (mast cell, basophil) bound IgE and mediator release, T-cell epitopes and IgE epitopes need to be dissected.

Vrtala et al., *J. Clin. Invest.* 99 [Seiberler et al., *EMBO J.* 13:3481, 1994] 1673-1681 (1997) and WO 99/16467 disclose a novel strategy of reducing the anaphylactic activity of the major birch allergen Bet v 1 by disrupting the three dimensional structure by expressing two parts of the Bet v 1 cDNA representing amino acids 1-74 and 75-160 in *Escherichia coli*. In contrast to the complete recombinant Bet v 1, the recombinant fragments showed almost no allergenicity. Both non-anaphylactic fragments induced proliferation of human Bet v 1-specific T cell clones, indicating that they harboured all dominant T cell epitopes and therefore could be used for safe and specific T cell immunotherapy. The success of this strategy was believed to be due to the fact that the Bet v 1 allergen possesses discontinuous (i.e. conformational) IgE epitopes rather than continuous IgE epitopes as is the case for many other allergens.

In contrast to the major birch allergen Bet v 1, the major timothy grass pollen allergen Phl p 6 contains continuous (sequential) IgE epitopes and would therefore not be susceptible to the above fragmentation strategy to reduce anaphylactic activity as outlined above.

SUMMARY OF THE INVENTION

The present invention provides a hypoallergenic immunogenic molecule derived from the Phl p 6 allergen, wherein the Phl p 6 molecule has an N-terminal and/or C-terminal deletion which makes the molecule at least lack IgE binding capacity.

The present invention also provides a hypoallergenic immunogenic combination of molecules derived from the Phl p 6 allergen, comprising (i) a Phl p 6 molecule having an N-terminal deletion which makes the molecule at least lack IgE binding capacity, and (ii) a Phl p 6 molecule having a C-terminal deletion which makes the molecule at least lack IgE binding capacity, which two molecules together contains the complete sequence of Phl p 6.

The present invention further provides a method for the hyposensitization of a mammal suffering from IgE mediated allergy against a protein allergen.

Figure 1:
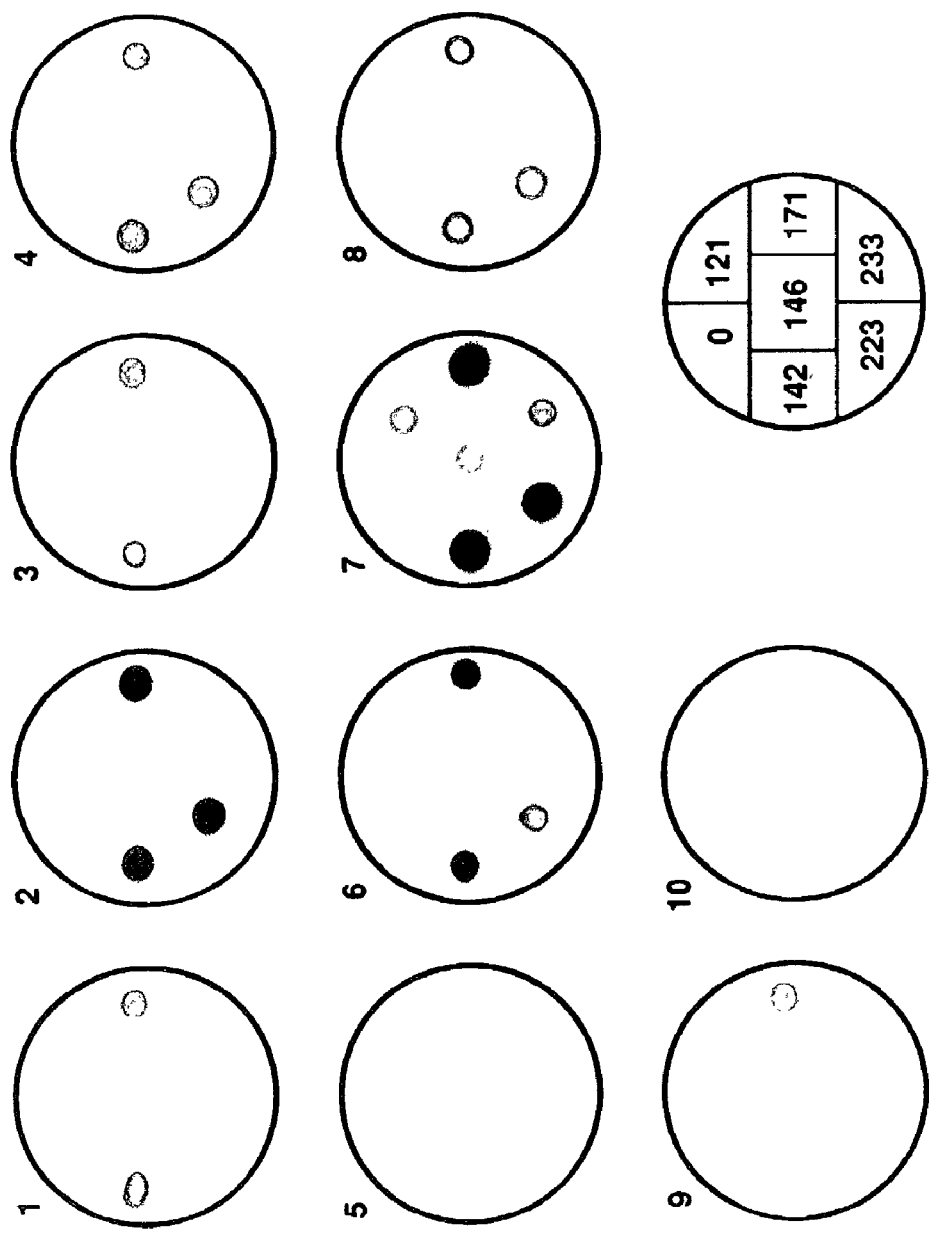
FIG. 1. IgE reactivity of rPhl p 6 isoforms and fragments. Nitrocellulose filters containing proteins from recombinant λgt 11 phage expressing two Phl p 6 isoforms (c142, c223), Phl p 6 fragments (c121, c146, c171, c233) and for control purposes, λgt11 wild type phage (0) were probed with serum IgE from 9 grass pollen-allergic patients (1-9) and from one non-allergic individual [Knox et al., Clin. Exp. Allergy 27:246, 1997].

TABLE 1. Immediate type skin reactivity to rPhl p 6. Four grass pollen allergic patients (HP, SF, CS, LW) and two non-allergic individuals (SV, SS) were skin tested with purified rPhl p 6, rPhl p 5, with natural timothy grass pollen extract, histamine and isotonic sodium chloride. Results are displayed as the mean diameters (mm) of the wheal reaction.

TABLE II. IgG-1-reactivity of mouse anti-rPhl p 6 or anti-rPhl p 6 aa 31 -110 antisera to rPhl p 6.

SEQUENCE LISTING

SEQ ID NO: 1—Artificial Primer (nucleotide sequence—29 residues)
SEQ ID NO: 2—Artificial Primer (nucleotide sequence—45 residues)
SEQ ID NO: 3—Artificial Primer (nucleotide sequence—29 residues)
SEQ ID NO: 4—Artificial Primer (nucleotide sequence—45 residues)
SEQ ID NO: 5—Phleum pratense (peptide sequence—4 amino acids)
SEQ ID NO: 6—Phleum pratense (peptide sequence—4 amino acids)
SEQ ID NO: 7—Phleum pratense (peptide sequence—4 amino acids)
SEQ ID NO: 8—full length recombinant Phl p6 (peptide sequence—138 amino acids)
SEQ ID NO: 9—full length c142 (nucleotide sequence—750 residues)
SEQ ID NO: 10—full length c223 (nucleotide sequence—571 residues)
SEQ ID NO: 11—full length c171 (nucleotide sequence—647 residues)
SEQ ID NO: 12—full length c121 (nucleotide sequence—572 residues)
SEQ ID NO: 13—full length c233 (nucleotide sequence—474 residues)
SEQ ID NO: 14—full length c146 (nucleotide sequence—554 residues)
SEQ ID NO: 15—c142 (peptide sequence—138 amino acids)
SEQ ID NO: 16—c223 (peptide sequence—138 amino acids)
SEQ ID NO: 17—c171 (peptide sequence—106 amino acids)
SEQ ID NO: 18—c121 (peptide sequence—80 amino acids)
SEQ ID NO: 19—c233 (peptide sequence—57 amino acids)
SEQ ID NO: 20—c146 (peptide sequence—53 amino acids)
SEQ ID NO: 21—recombinant Phl p6 (28 aa hydrophobic leader peptide and amino acids 1-29)
SEQ ID NO: 22 - recombinant Phl p6 (amino acids 1-57)

DETAILED DESCRIPTION OF THE INVENTION

The present invention has surprisingly and most unexpectedly been found that Phl p 6 deletion variants may be constructed by genetic (recombinant) or synthetic fragmentation, which fragments may be used for specific immunotherapy of grass pollen allergy with reduced anaphylactic side effects. Such fragments with strongly reduced anaphylactic ability will below be referred to as non-anaphylactic or hypoallergenic.

In a first aspect of the present invention there is provided a hypoallergenic immunogenic molecule derived from the Phl p 6 allergen, wherein the Phl p 6 molecule has an N-terminal and/or C-terminal deletion which makes the molecule at least substantially lack IgE binding capacity.

The N-terminal or C-terminal deletion may be a terminal truncation of the allergen. The deletion may also be internal within the N-terminal or C-terminal part of the allergen, respectively.

The allergen molecule fragments may be produced by recombinant DNA techniques or peptide synthetic chemistry as is per se well known to the skilled person.

In a second aspect, the present invention provides a hypoallergenic immunogenic combination of molecules derived from the Phl p 6 allergen, comprising (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete amino acid sequence of the Phl p 6 allergen.

For together encompassing the complete amino acid sequence of Phl p 6, the respective sequences of the two Phl p 6 molecules may overlap or be contiguous.

The sizes of the N-terminal and C-terminal deletions of the Phl p 6 allergen necessary for the fragments to be useful for the purposes of the invention, i.e. that the fragments are (i) immunogenic and (ii) non-IgE reactive, may readily be determined by the skilled person. Thus, the lack or presence of IgE binding ability of a particular N-terminal or C-terminally deletion molecule may easily be determined, the lack of IgE reactivity indicating that the molecule may be applied without or with low risk of inducing anaphylactic side effects. Immunogenic activity of the molecules may be determined by their capability of being recognized by a polyclonal antiserum to the complete Phl p 6 allergen. In this way fragments and fragment combinations, respectively, may be selected which have a very high likelyhood of being capable of eliciting immune responses which protect against the complete allergen.

A third aspect of the invention is a specific hyposensitization therapy. Such therapy may be performed as known in the art for protein allergens and encompasses administering repeatedly to the mammal, typically a human individual, suffering from type I allergy against the allergen an immunogen that is capable of raising an IgG immune response against the allergen. The immunogen may be admixed with suitable adjuvants such as aluminium oxide. Administration may be done systemically, for instance by injection, infusion, etc, but also the oral route has been suggested in order to expose the intestinal part of the immune system. See also Norman PS, "Current status of immunotherapy for allergies and anaphylactic reactions" *Adv. Internal. Medicine* 41 681-713 (1996).

Here, the immunogen to be administered may be an immunogenic molecule according to the first aspect of the invention, or a mixture of such molecules, preferably, the above-mentioned hypoallergenic immunogenic combination of molecules derived from the Phl p 6 allergen according to the second aspect of the invention, i.e. (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete amino acid sequence of Phl p 6.

More specifically, the immunogens may be used to induce antibody responses in a patient, and/or to elicit T cell response, and/or to modulate antibody and T cell repsonse to induce tolerance.

A fourth aspect of the present invention provides the use the immunogen according to the first aspect, or the combination of immunogens according to the second aspect, as an antigen in an immunoassay for detecting specific antibodies of the IgA, IgD, IgE, IgG or IgM class directed against the Phl p 6 allergen from which the immunogen(s) derive. Appropriate assay variants involve formation of a ternary immune complex between the immunogen, sample antibody and an antibody directed against the Ig-class of interest. The sample may be any Ig-containing biological fluids, for instance a blood derived sample (serum, plasma, whole blood), CSF, etc. Especially, the hypoallergenic fragments may be used for diagnostic monitoring (e.g. IgG measurements, measurement of T cell responses) during therapy when inducing a new immune response against the fragments.

The invention will now be illustrated by the following Examples.

EXAMPLES

Biological Materials, Patients Sera, Antisera, Recombinant Allergens.

Pollen from timothy grass (*Phleum pratense*), rye grass (*Lolium perenne*), rye (*Secale cereale*), Kentucky blue grass (*Poa pratensis*), wheat (*Triticum sativum*), cultivated oat (*Avena sativa*) and common reed (*Phragmites communis*) were from Allergon AB, (Välinge, Sweden). Timothy grass seeds were purchased from Austrosaat, (Vienna, Austria) and grown for 4 weeks to obtain fresh leaves and roots. Patients allergic to grass pollen were characterized as described [Niederberger et al., *J. Allergy Clin. Immunol.* 101:258, 1998]. The rabbit anti-celery profilin antiserum (RP1) is described [Vallier et al., *Clin. Exp. Allergy* 22:774, 1992]. A rabbit anti-rPhl p 6 antiserum was raised against purified, recombinant Phl p 6 using Freunds adjuvans (Charles River, Kissleg, Germany). Recombinant timothy grass pollen allergens, rPhl p 1, rPhl p 2 and rPhl p 5 were purified as described [Vrtala et al., *J. Allergy Clin. Immunol.* 97:781, 1996]. Recombinant timothy grass pollen profilin was purified by poly (L-proline) affinity chromatography [Valenta et al., *Science* 253:557, 1991].

Isolation and Characterization of cDNAs Coding for Phl p 6 Isoforms/fragments.

Three hundred and fifty IgE-reactive clones were isolated from an expression cDNA library constructed from mature timothy grass pollen in phage λgt 11 [Vrtala et al., *J. Immunol.* 151:4773, 1993]. Six cDNAs: [(]c121 (SEQ ID NO: 9), c142 (SEQ ID NO: 10), c146 (SEQ ID NO: 11), c171 (SEQ ID NO: 12), c223 (SEQ ID NO: 13), c233 (SEQ ID NO: 14) with sequence homology to a Phl p 6-encoding cDNA [Peterson et al., *Int. Arch. Allergy Immunol.* 108:55, 1995] were subcloned into plasmid pUC18 and sequenced [Sambrook et al., *Molecular cloning: A Laboratory Manual*, (1989); Sanger et al., *Proc. Natl. Acad. Sci. USA* 74:5463 (1977)]. Sequences were analyzed using the McVector program (Kodak, Rochester, N.Y.). Search for Phl p 6-homologous protein sequences was done with the FastA program (GCG package) [Devereux et al., *Nucl Acids Res.* 12:387, 1984] in the SwissProt database. The sequences of Hol l 5 and Hor v 5 allergens were retrieved from the EMBL database. Multiple sequence alignment was produced with ClustalW [Thompson et al., *Nucl. Acids Res.* 22:4673, 1994] and edited by hand. The GDE sequence editor (S. Smith, Harvard University, Cambridge, Mass.) and COLORMASK (J. Thompson, EMBL, Heidelberg, Germany) were used to color conserved residues with related properties [Thompson et al., *Nucl. Acids Res.* 22:4673, 1994]. Protein secondary structure and surface accessibility predictions were done with the PHD program on the EMBL PredictProtein server [Rost et al., *J. Mol. Biol.* 232:584, 1993].

Mapping of Phl p 6 IgE Epitopes, Expression and Purification of Recombinant Phl p 6.

The IgE binding capacity of phage clones expressing Phl p 6 isoforms and fragments was investigated by a plaque lift assay [Ball et al., *J. Biol. Chem.* 269:28323, 1994]. The DNA coding for the mature Phl p 6 allergen was PCR-amplified from the clone 142 DNA, subcloned into the NdeI/Eco RI site of pET-17b. Recombinant Phl p 6 was expressed in *E. coli* BL 21 (DE 3) in liquid culture. Cells were suspended in 25 mM Imidazole, pH 7.4, 0.1% Triton X-100 and lysed by addition of lysozyme (20 µg/g cells) for 30 minutes at room temperature as well as by freeze-thawing cycles. DNA was digested with DNAse I (0.1 mg/g cell pellet) for 20 minutes at room temperature. The protein extract was centrifuged for 20 min at 10.000× g (Sorvall RC5C; SS34 rotor) to remove insoluble materials. rPhl p 6 was enriched in a precipitate obtained by addition of ammonium sulfate (40-60% w/v). The precipitate was dissolved in 10 mM Tris pH 6, dialyzed against this buffer and after centrifugation (20 min, 10.000 g, Sorvall RC5C; SS34 rotor) was applied to a diethylaminoethyl cellulose-Sepharose column (Pharmacia). Unbound proteins were eluted with 10 mM Tris, pH 6, 4% v/v isopropanol. Fractions containing more than 80% pure Phl p 6 were adjusted to pH 8 with NaOH and subjected to a second chromatography step on a diethylaminoethyl cellulose-Sepharose column. Elution of bound proteins with a 0-0.5 M NaCl gradient at pH 8 yielded fractions containing pure rPhl p 6 which were dialyzed against $H_2O_{dd}$.

MALDI-TOF (Matrix Assisted Laser Desorption and Ionisation—Time Offlight) and CD (Circular Dichroism) Analysis of Purified Recombinant Phl p 6.

Laser desorption mass spectra were acquired in a linear mode with a time-of-flight Compact MALDI II instrument (Kratos, Manchester, UK) (piCHEM, Graz, Austria). CD spectra were recorded on a Jasco J-710 spectropolarimeter fitted with a Jasco PTC-348WI peltier type temperature control system and interfaced with a Fisons HAAKE GH water bath. Far ultraviolet CD spectra were recorded at 20° C. in a 2 mm path-length quartz cuvette (Hellma, Mullheim, Baden, Germany) at a protein concentration of 7 µM. Thermal denaturation of Phl p 6 was monitored by recording the ellipticity during temperature increase (50° C./h) at 220 nm. The reversibility of the unfolding process was checked by measuring the restoration of the CD signal upon cooling (50° C./h) to the starting temperature (20° C.). The fraction of folded protein was calculated as $F=1-U$, where $U=(\Theta_{220}-\Theta_N)/(\Theta_U-\Theta_N)$. $\Theta_N$ is the ellipticity of the protein in the native state and $\Theta_U$ that of the denatured protein. For rPhl p 6, $\Theta_U$ was assumed to be equal to $\Theta_{220}$ at 85° C. and $\Theta_N$ to $\Theta_{220}$ at 20° C.

IgE-binding Capacity of Recombinant Phl p 6, Cross-Reactivity with Natural Phl p 6 and other Timothy Grass Pollen Allergens.

The prevalence of IgE anti-rPhl p 6 reactivity was determined in sera from 171 grass pollen allergic patients and, for control purposes, in sera from non-atopic persons by ELISA [Vrtala et al., *J. Allergy Clin. Immunol.* 97:781, 1996]. The presence of cross-reactive IgE epitopes on natural and rPhl p 6 was investigated by IgE immunoblot inhibition experiments [Niederberger et al., *J. Allergy Clin. Immunol.* 101:258, 1998]. A possible immunological relationship between rPhl p 6 and recombinant timothy grass pollen allergens (rPhl p 1, rPhl p 2, rPhl p 5) [Vrtala et al., *J. Allergy Clin. Immunol.* 97:781, 1996] was studied by ELISA competition as described [Niederberger et al., *J. Allergy Clin. Immunol.* 101: 258, 1998].

Histamine Release Experiments.

Granulocytes were isolated from heparinized blood samples of grass pollen allergic individuals containing rPhl p 6-reactive IgE antibodies by dextran sedimentation [Valent et al., *PNAS USA* 86:5542, 1989]. Cells were incubated with increasing concentrations of purified rPhl p 5, rPhl p 6, and with an anti-human IgE antibody (E124.2.8 Dε2, Immunotech, Marseille, France). Histamine released into the supernatants was measured by radioimmunoassay (Immunotech, Marseille, France).

Skin Testing.

After informed consent was obtained skin prick tests were performed on the forearms of the individuals as described [Vrtala et al., *J. Clin. Invest.* 99:1673, 1997]. Individuals were pricked with 20 µl aliquots containing different concentrations (1 µg/ml, 10 µg/ml, 100 µg/ml) of purified rPhl p 6, rPhl p 5 and with timothy grass pollen extract, histamine and sodium chloride (ALK, Horsholm, Denmark).

Analysis of the Presence of Phl p 6-related Allergens in other Grass Species and Tissue-Specific Expression of Phl p 6.

Protein extracts from pollens, leaves and roots were obtained by homogenizing the tissues in SDS-sample buffer [Laemmli, U. K., *Nature* 227:680, 1970]. Insoluble materials were removed by centrifuging the extracts (10,000× g, 20 min; Sorvall RC5C, SS34 rotor). Protein extracts were separated by 14% SDS-PAGE [Fling et al., *Anal. Biochem.* 155: 83, 1986] and blotted onto nitrocellulose [Towbin et al., *PNAS USA* 76:4350]. Nitrocellulose strips were probed with a rabbit anti-celery profilin antiserum, RP1, [Vallier et al., *Clin. Exp. Allergy* 22:774, 1992], the rabbit anti-rPhl p 6 antiserum and the latter rabbits preimmune serum. Bound rabbit antibodies were detected with a 1:1000 diluted $^{125}$I-labeled donkey anti-rabbit Ig antiserum (Amersham).

In Situ Localization of Phl p 6 by Immunogold Electron Microscopy.

Timothy grass pollen grains were unhydrously fixed as described [Grote et al., *J. Histochem. Cytochem.* 42:427, 1994]. Ultrathin sections were incubated with equal concentrations of either rabbit anti-rPhl p 6 Ig (Ig: protein G-purified immunoglobulin fraction) or preimmune Ig. Bound rabbit antibodies were detected with goat anti-rabbit IgG antibodies coupled to 10 nm colloidal gold particles (Piano, Wetzlar, Germany) [Grote et al., *J. Histochem. Cytochem.* 42:427, 1994].

Construction of Hypoallergenic Phl p 6 (*Phleum pratense*) Deletion Variants.

N-terminal and C-terminal Phl p 6 deletion variants were generated to represent aa 31-110 and aa 1-57. cDNAs coding for Phl p 6 aa 31-110 and Phl p 6 aa 1-57 were obtained by PCR amplification of the Phl p 6 cDNA (clone #142) using the following oligonucleotide primers:

```
For Phl p 6 aa 1-57:
5': GGG AAT TCC ATA TGG GGA AGG CCA CGA CC 3'                               (SEQ ID NO:1)
5': CGG GGT ACC CTA GTG GTG GTG GTG GTG GTG GGG CGC CTT TGA AAC 3'          (SEQ ID NO:2)

For Phl p 6 aa 31-110:
5': GGG AAT TCC ATA TGG CAG ACA AGT ATA AG 3'                               (SEQ ID NO:3)
5': CCG GAA TTC CTA GTG GTG GTG GTG GTG GTG CGC GCC GGG CTT GAC 3'          (SEQ ID NO:4)
```

Eco R I and Kpn I sites are printed in italics, Nde I sites and a His-tag, which has been introduced at the C-terminus, are underlined.

The PCR-products were cut with Nde I/Kpn I (aa 1-57) or with Nde I/Eco R I (aa 31-110), purified by preparative agarose gel electrophoresis, subdloned into plasmid pET-17b (Novagen) and transformed into *E. coli* BL 21(DE3) (Novagen). Colonies expressing the correct deletion variants were identified by immunoscreening using a rabbit anti-Phl p 6 antiserum. DNA from positive clones was isolated using Qiagen tips (Qiagen, Hilden, Germany) and sequenced (MWG-Biotech, Hilden, Germany).

Expression of Phl p 6 Deletion Variants in *E. coli* and Testing of their IgE-binding Capacity Recombinant Phl p 6 aa 1-57 and Phl p 6 aa 31-110 were expressed in *E. coli* B1 21 (DE 3) by induction with 0.5 mM isopropyl-β-thiogalactopyranoside at an $OD_{600}$ of 0.8 in liquid culture for 5 h at 37° C. Equal amounts of rPhl p 6, rPhl p 6 aa 1-57 and rPhl p 6 aa 31-110 were separated by SDS-PAGE and blotted onto nitrocellulose.

Nitrocellulose strips were incubated with serum IgE from allergic individuals, nonallergic control persons, with a rabbit anti-Phl p 6 antiserum and a rabbit preimmunserum. Bound IgE antibodies were detected with $^{125}$I-labeled anti-human IgE antibodies and bound rabbit antibodies with $^{125}$I-labeled donkey anti-rabbit antibodies.

Isolation and Characterization of cDNAs Coding for Isoforms/fragments of Phl p 6.

Six cDNA clones: c142 (SEQ ID NO: 9), c223 (SEQ ID NO: 10), c171 (SEQ ID NO: 11), c121 (SEQ ID NO: 12), c233 (SEQ ID NO: 13), c146 (SEQ ID NO: 14), coding for Phl p 6 isoforms/fragments were isolated from a timothy grass pollen λgt11 library with serum IgE from a grass pollen allergic patient. The sequences of the described clones have been deposited in the GenBank database (Accession numbers: Y16955-Y16960). The deduced amino acid sequence of Phl p 6 (clone 142) contained a 28 aa hydrophobic leader peptide. A molecular mass of 11.8 kDa and a pI of 5.5 were calculated for the mature Phl p 6 (clone 142) protein which starts with a glycine residue and shows a high content of alanine residues (20.9%). The computer-aided secondary structure analysis of Phl p 6 indicates a predominant helical content and the calculation of solvent accessibility predicts that many of the N-terminal amino acids are solvent exposed while most of the C-terminal amino acids appeared buried. A search for sequence motifs revealed the presence of one potential N-linked glycosylation site (NAS: aa 15-17), one N-terminal myristoylation site (GKAT(SEQ ID NO: 5): aa 1-4), two cAMP-dependent protein kinase phosphorylation sites (KATT(SEQ ID NO: 6): aa 2-5; KYKT(SEQ ID NO: 7): aa 33-36) and two peroxisomal targeting sequences (GKA: aa 1-3; SKA: aa 54-56). The deduced Phl p 6 amino acid sequence displayed identity with a recently submitted Phl p 6 sequence [Peterson et al., *Int. Arch. Allergy Immunol.* 108:55, 1995] and similarities with the N-terminal portions of group 5 grass pollen allergens. However, Phl p 6 specific IgE shows little or no crossreactivity with group 5 allergens. A comparison with group 5 grass pollen allergens is given in Vrtala, S., et al., *J. Immunol.* 1999, 163 [Knox et al., *Clin. Exp. Allergy* 27:246, 1997]: 5489-5496 [Vrtala et al., *J. Immunol.* 163: 5489, 1999] (the disclosure of which is incorporated by reference herein). FIG. 1A therein shows a multiple sequence alignment, secondary structure and solvent accessibility prediction of Phl p 6 variants and group 5 allergens.

The Phl p 6 N-terminus is Relevant for IgE Binding.

Nitrocellulose-bound β-gal-fused complete (c223, c142), N-terminally truncated rPhl p 6 (c171, c121, c233, c146) and, for control purposes, β-gal alone were exposed to serum IgE from 9 grass pollen allergic individuals and a non-allergic person (FIG. 1). Results obtained showed that the two complete Phl p 6 isoforms and a Phi p 6 fragment lacking only 4 of the N-terminal amino acids strongly bound IgE from all grass pollen allergic patients tested and that the IgE binding capacity of the partial Phl p 6 clones decreased depending on the number of amino acids which were absent from the proteins' N-terminus. A partial clone (clone 121) lacking the N-terminal 30 amino acids had almost completely lost its IgE binding capacity (FIG. 1).

Figure 2A:
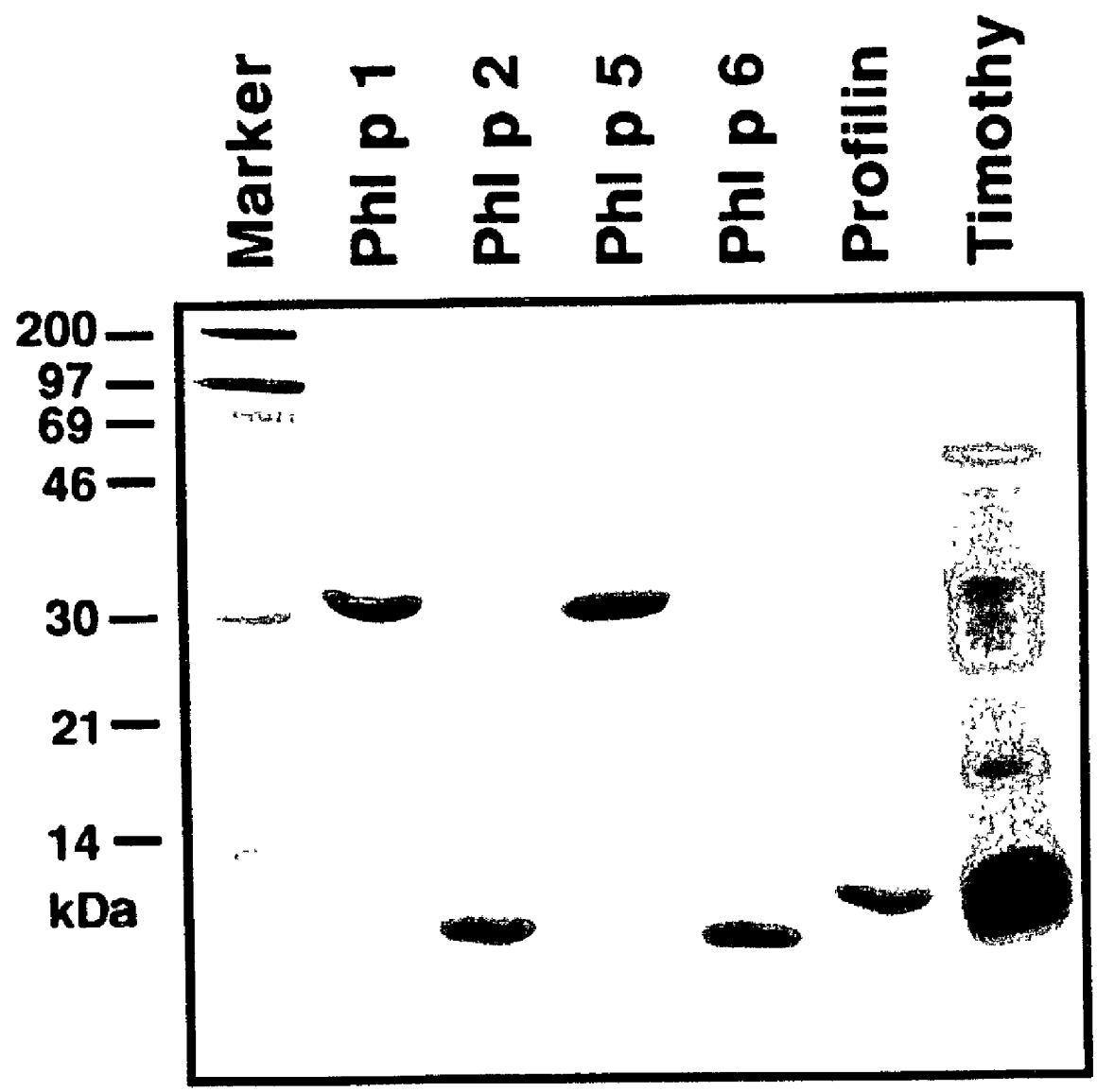
FIG. 2. A, Purity of recombinant timothy grass pollen allergens. Coomassie brilliant blue-stained SDS-PAGE containing purified, recombinant timothy grass pollen allergens (Phl p 1, Phl p 2, Phl p 5, Phl p 6, timothy grass pollen profilin) and natural timothy grass pollen extract (Timothy). (M) Molecular weight marker. B, C Circular dichroism analysis. B, Far-UV circular dichroism spectra of rPhl p 6, expressed as mean residue ellipticity ([Θ]) (y-axis), were recorded in the wavelength range displayed on the x-axis at 20° C. (continuous line), 85° C. (dotted line) and at 20° C. after cooling from 85° C. (dashed line). C, Thermal denaturation and cooling of purified rPhl p 6 monitored at 220 nm (x-axis: temperature in ° C.; y-axis: apparent fraction of the folded protein).

*E. coli* Expression and Purification of Recombinant Phl p 6. IgE Binding Capacity of Purified rPhl p 6.

rPhl p 6 was overexpressed in *E. coli* BL21 (DE3). A combination of several purification steps yielded pure and soluble rPhl p 6 (approximately 5mg protein/liter *E. coli* culture) which by SDS-PAGE was identified as one of the low molecular weight timothy grass pollen allergens (FIG. 2A). MALDI-TOF analysis of purified recombinant Phl p 6 resulted in two mass/charge peaks of 11790 and 5896 corresponding to the MH+ and M2H2+ species of the sample which were in agreement with the deduced Phl p 6 molecular mass (11789 Da).

In 128 sera from 171 grass pollen allergic patients but in no serum from 10 non-allergic individuals rPhl p 6-specific IgE antibodies were detected. Preabsorption of sera from grass pollen allergic patients with rPhl p 6 led to a great reduction of IgE binding to a 10-14 kDa moiety in nitrocellulose-blotted timothy grass pollen extract indicating that rPhl p 6 and natural Phl p 6 share IgE epitopes. ELISA competition experiments demonstrated that only a small percentage (<20%) of Phl p 5-specific IgE could be preabsorbed with rPhl p 6. IgE binding to rPhl p 1, rPhl p 2 and recombinant timothy grass profilin was not reduced after preincubation of sera with rPhl p 6. These results identify Phl p 6 as a major allergen which is distinct from other grass pollen allergens.

rPhl p 6 Folds in a Stable all Alpha Helical Conformation.

Figure 2B:
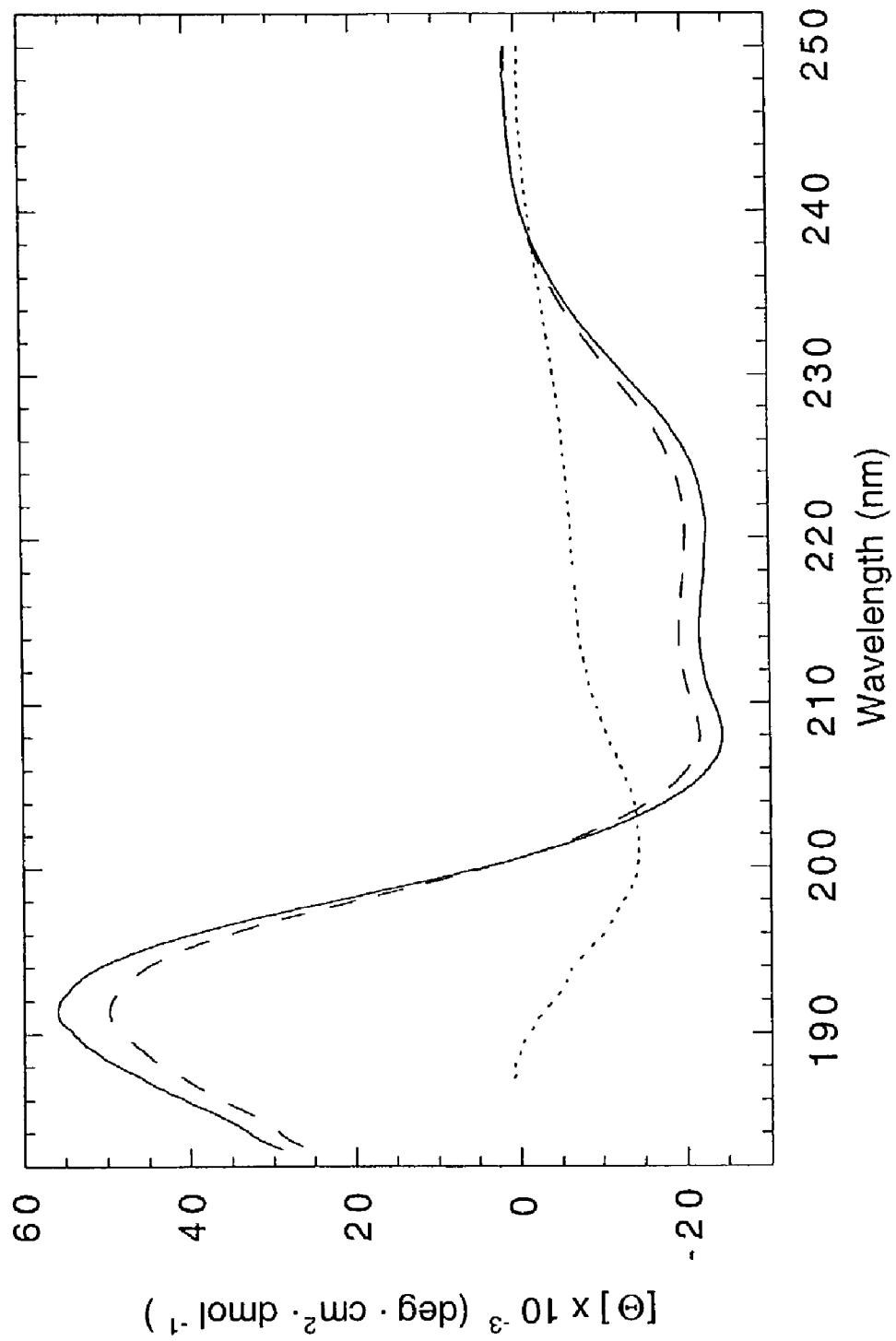
Figure 2C:
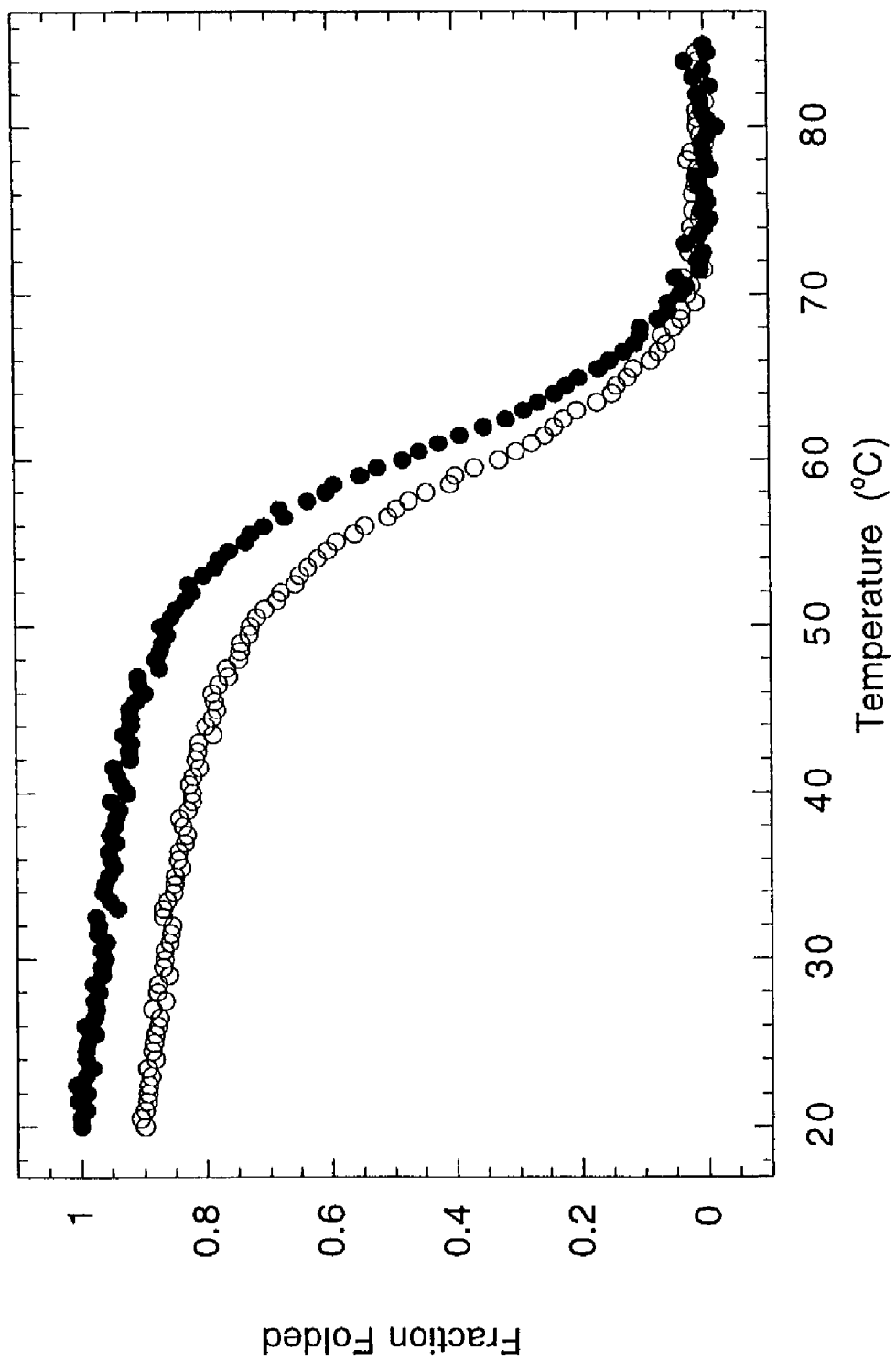

The far-ultraviolet CD spectrum of purified rPhl p 6 (FIG. 2B) indicates that the protein contains a considerable amount of alpha-helical secondary structure. The spectrum is characterized by two broad minima at 208 nm and 220 nm and a maximum at 1 is in good agreement with the CD measurements as it indicates predominant alpha helical secondary structure content. The unfolding transition of rPhl p 6 is monophasic and highly cooperative with a melting point of 61° C. At 85° C., rPhl p 6 assumes a random coil conformation, with a typical minimum at 200 nm. rPhl p 6 shows a high degree of folding reversibility, evident from the cooling curve profile (FIG. 2C) and the far-UV spectrum recorded at 20° C. after cooling from 85° C. (FIG. 2B).

Recombinant Phl p 6 Induces Dose Dependent Basophil Histamine Release and Immediate Type Skin Reactions in Grass Pollen Allergic Patients.

Figure 3A:
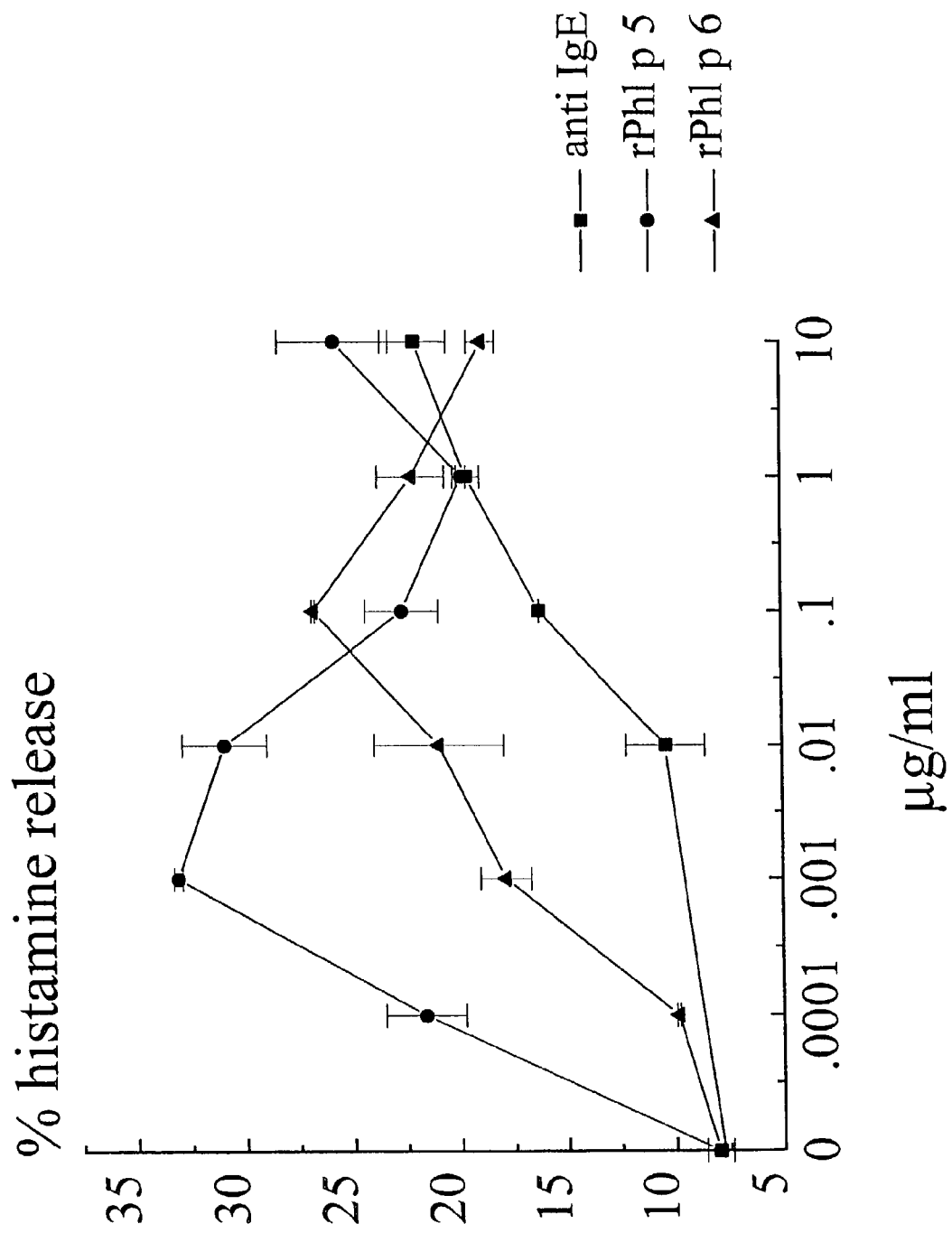
FIG. 3. A, rPhl p 6 induces basophil histamine release. Granulocytes from a grass pollen allergic patient were incubated with various concentrations (x-axis) of purified, recombinant Phl p 6 (triangles), Phl p 5 (points) or a monoclonal anti-IgE antibody (squares). The percentage of histamine released into the supernatant is displayed on the y-axis. Results represent the means (+/− SD) of triplicate determinations. B, Induction of immediate type skin reactions with rPhl p 6 in sensitized allergic patients. Two grass pollen allergic patients (a) LW, (b) HP and a non-allergic individual (c) SV were pricked on their forearms with increasing concentrations of rPhl p 6 and rPhl p 5 as well as with histamine (Hist) and NaCl as indicated in (d). The wheal area was surrounded with a ball point pen.
Figure 3B:
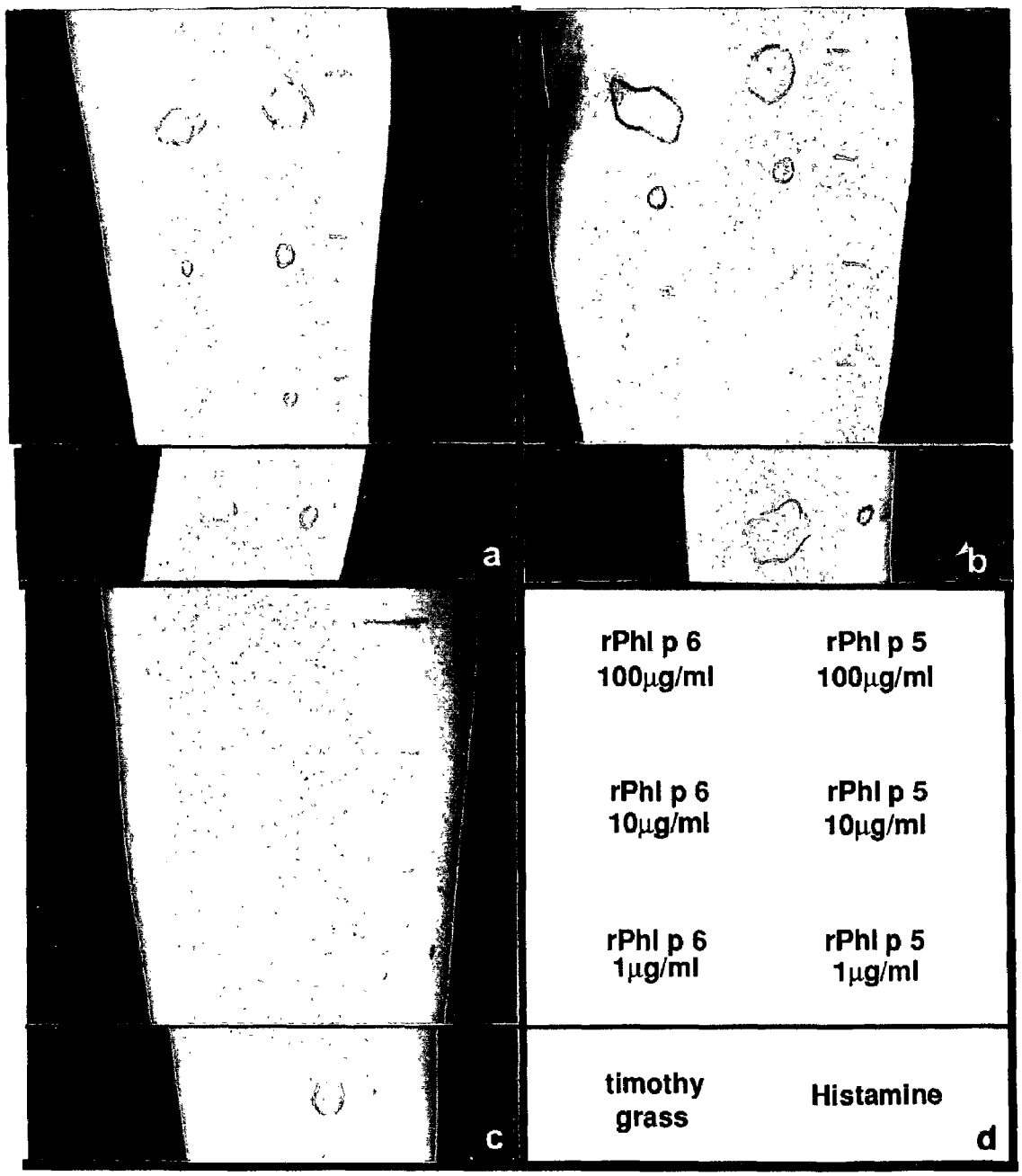

Purified rPhl p 6 induced specific and dose-dependent histamine release from basophils of a grass pollen allergic patient (FIG. 3A). rPhl p 5 which represents a highly active grass pollen allergen (14, Valenta and Flicker, unpublished data) induced maximal release already at a lower concentration compared to rPhl p 6. In four grass pollen allergic patients but not in the non-allergic individuals, rPhl p 6, rPhl p 5 and timothy grass pollen extract induced immediate type skin reactions (Table 1; FIG. 3B). While no reactions to sodium chloride were observed, histamine induced wheal reactions in all individuals tested (Table 1; FIG. 31B).

Group 6 Allergens Represent Pollen-Specific Proteins.

Figure 4:
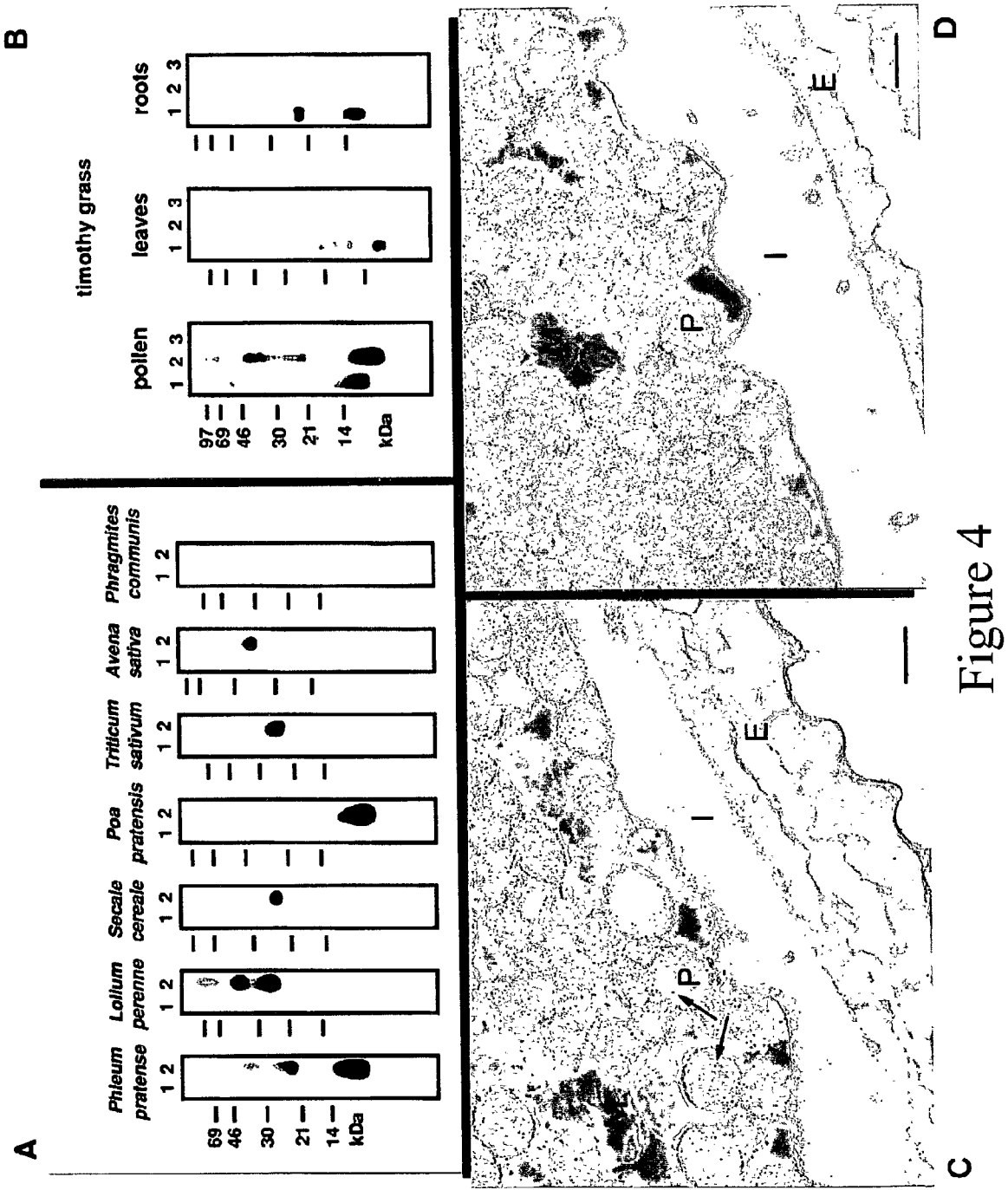
FIG. 4. Tissue-specific expression of Phl p 6. A, Nitrocellulose-blotted grass pollen extracts from various monocots were probed with rabbit preimmune Ig (lanes 1) or rabbit anti-rPhl p 6 Ig (lanes 2). B, Comparable amounts of nitrocellulose blotted protein extracts from timothy grass pollen, leaves and roots were incubated with rabbit anti-profilin Ig (lanes 1), rabbit anti-Phl p 6 Ig (lanes 2) or rabbit preimmune Ig (lanes 3). C, D, Ultrastructural localization of Phl p 6. Ultrathin sections of timothy grass pollen were stained with rabbit anti-Phl p 6 Ig (C) and with rabbit preimmune Ig (D). Bound rabbit antibodies were detected with a gold-conjugated goat anti-rabbit Ig antiserum (gold particles = black dots). Arrows indicate Phl p 6 immunoreactivity on the P-particles. Abbreviations: E: exine; I: intine; P: P-particle. The bars represent 0.250 μm.

While major groups of grass pollen allergens occur in pollens of most grass species [Niederberger et al., *J. Allergy Clin. Immunol.* 101:258, 1998], group 6 allergens were reported to occur exclusively in timothy grass (*Phleum pratense*) pollen [Peterson et al., *Int. Arch. Allergy Immunol.* 108:55, 1995]. A rabbit anti-rPhl p 6 antiserum cross-reacted with group 5 allergens in nitrocellulose blotted pollen extracts from various monocots (*Phleum pratense, Lolium perenne, Secale cereale, Triticum sativum, Avena sativa, Phragmites communis*) between 25-28 kDa (FIG. 4A, lanes 2). Phl p 6 or Phl p 6-related allergens at 11 kDa were detected exclusively in pollens from *Phleum pratense* and *Poa pratensis*. Although a putative N-glycosylation site was found in the amino acid sequence deduced from the Phl p 6 CDNA sequence, comparable molecular weights observed for natural and recombinant Phl p 6 exclude heavy glycosylation of natural Phl p 6 (FIGS. 4A, 2A). Rabbit anti-rPhl p 6 antibodies strongly reacted with Phl p 6 at 11 kDa in nitrocellulose-blotted timothy grass pollen but not with leaf or root extracts (FIG. 4B, lanes 2). Profilin was detected in all three tissues at approximately 14 kDa (FIG. 4B, lanes 1).

Immunelectronmicroscopical Localization of Phl p 6 in Timothy Grass Pollen.

Using post-embedding immunogold electron microscopy, rabbit anti-rPhl p 6 antibodies bound to the numerous polysaccharide (P-) particles which fill much of the interior of a mature timothy grass pollen grain (FIG. 4C). The greatest accumulation of gold particles was observed on sectioned surfaces of the P-particles indicating that Phl p 6 is present on rather than in the P-particles. Little (cytosol, exine) or no (mitochondria, intine) anti-rPhl p 6 immunoreactivity was observed in other parts of the pollen grain. Likewise almost no gold particles were detected in the amyloplasts. This localization pattern, taken together with our finding that a rabbit anti-rPhl p 5 antiserum failed to label the P-particles (data not shown) excludes the possibility that the immunolabeling of the P-particles resulted from the presence of cross-reactive group 5 allergens. Control experiments performed with pre-immune Ig yielded only a few non-specifically adsorbed gold particles (FIG. 4D).

Phl p 6 Deletion Variants (aa 1-57, aa 31-110) Exhibit Strongly Reduced IgE Binding Capacity.

Figure 5A:
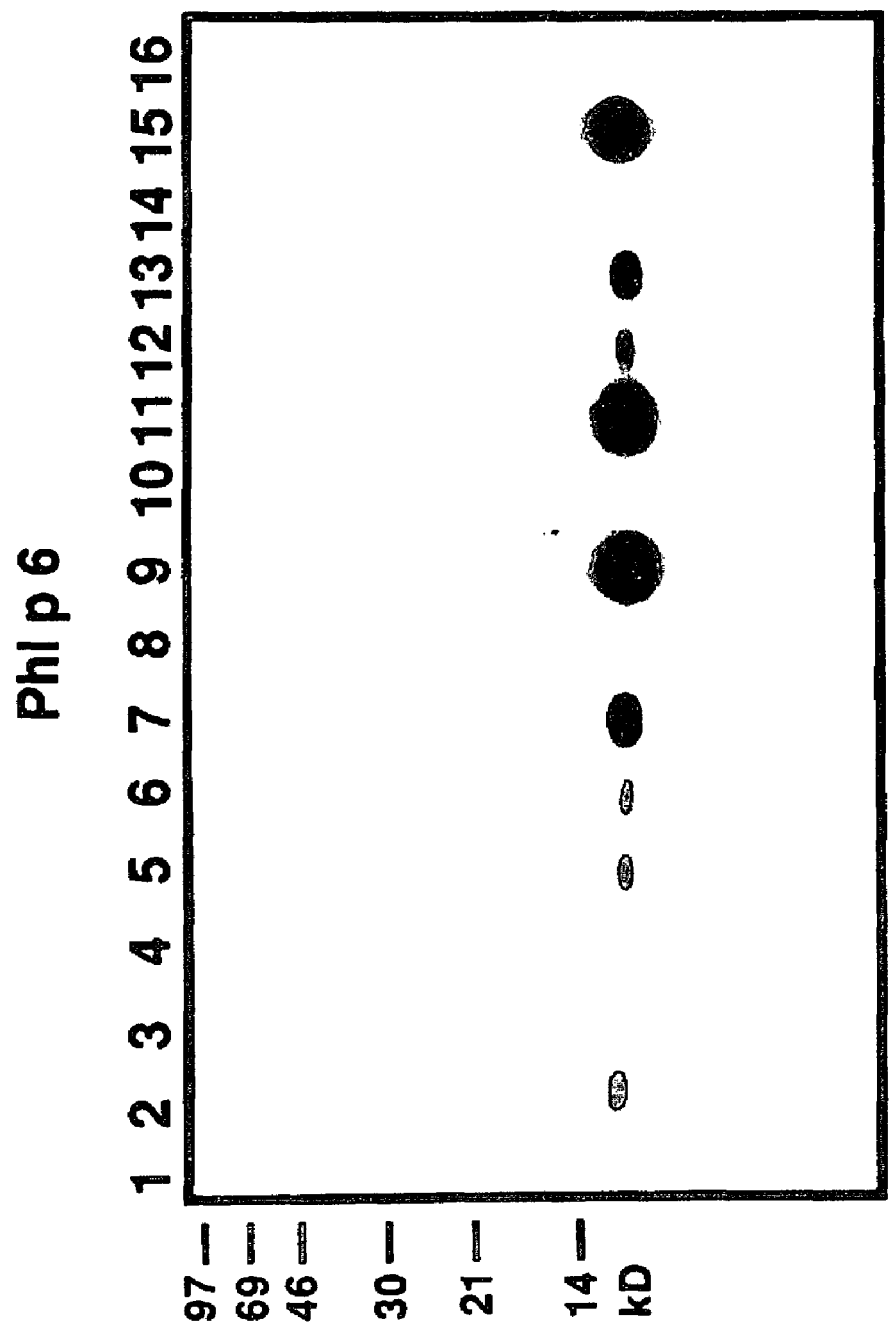
FIG. 5. Reduced IgE binding capacity of Phl p 6 deletion variants Equal amounts of recombinant Phl p 6 (A), Phl p 6 aa 1-57 (B) and Phl p 6 aa 31-110 (C) were tested for IgE-reactivity with sera from timothy grass pollen allergic patients (lane 1-13) and serum from a non-allergic control individual (lane 14). Lane 15 and lane 16 show the reactivity with a rabbit anti-Phl p 6 antiserum and a rabbit preimmunserum. Bound IgE antibodies were detected with $^{125}$I-labeled anti-human IgE antibodies, bound rabbit antibodies with $^{125}$I-labeled donkey anti-rabbit antibodies and visualized by autoradiography.
Figure 5B:
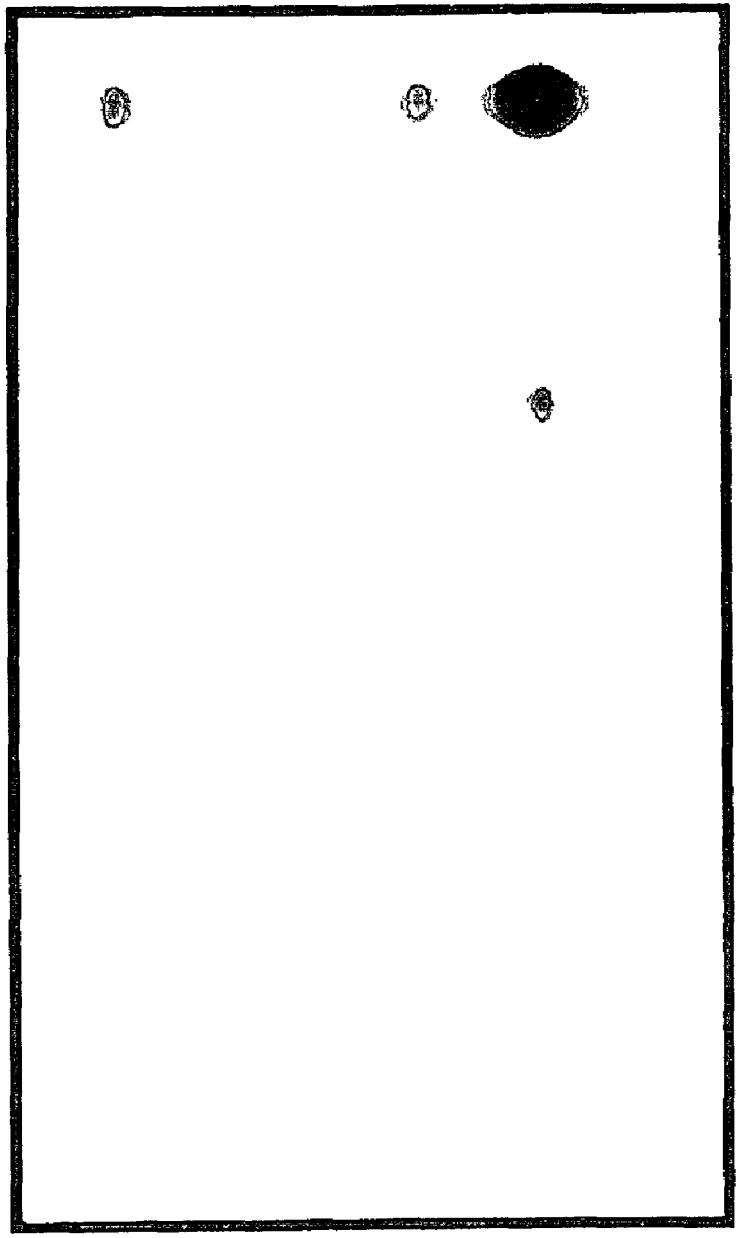
Figure 5C:
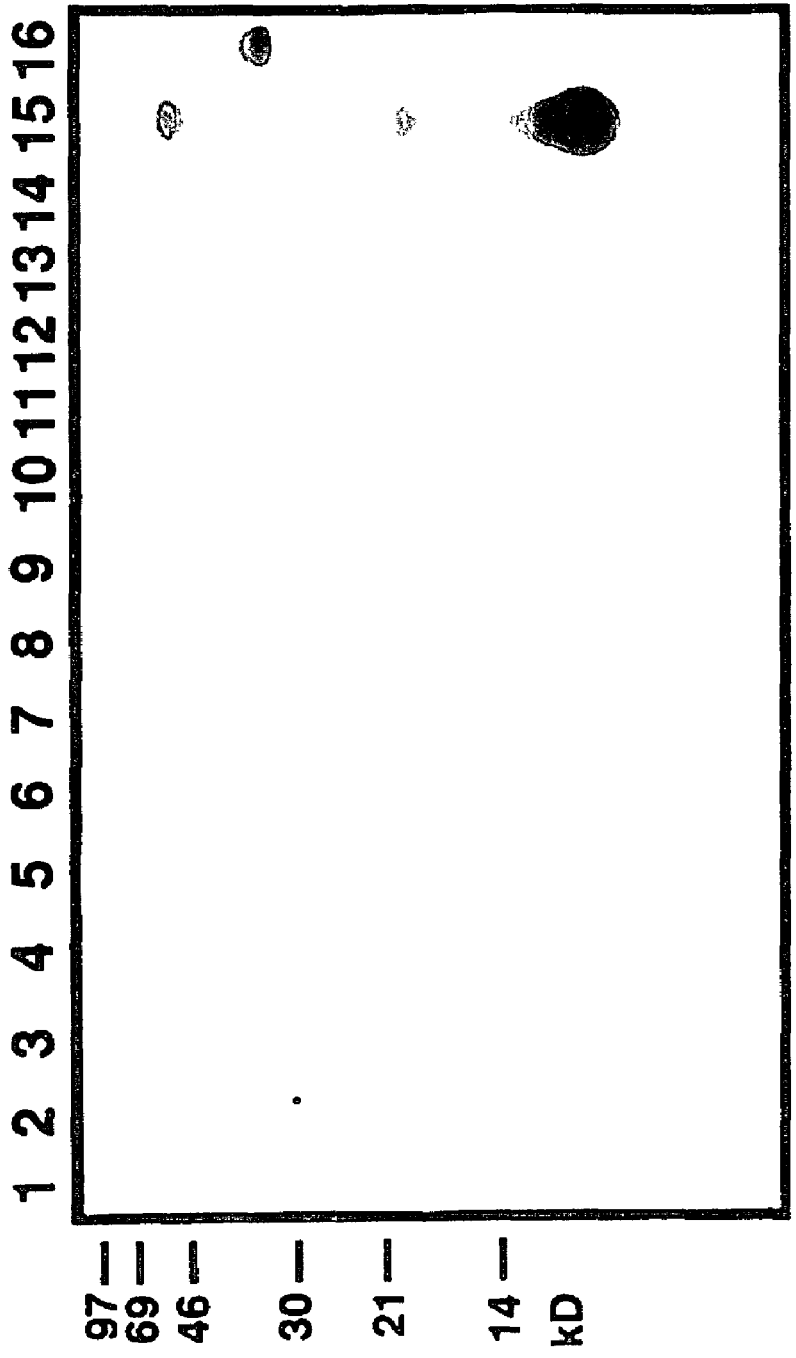

Nitrocellulose-blotted complete rPhl p 6 (FIG. 5A), rPhl p 6 variant aa 1-57 (FIG. 5B) and rPhl p 6 variant aa 31-110 (FIG. 5C) were exposed to 13 sera from grass pollen allergic patients, to a serum from a non-atopic person and to a rabbit anti-rPhl p 6 antiserum. While all 13 grass pollen allergic patients displayed IgE reactivity to complete recombinant Phl p 6 (FIG. 5A), variant aa 1-57 was recognized by serum 11 and weakly by serum 13 (FIG. 5B). Phl p 6 variant aa 31-110 reacted only weakly with serum 7 and 11 (FIG. 5C). Serum from the non-atopic individual failed to react with complete rPhl p 6 and the deletion variants. The rabbit anti-rPhl p 6 antiserum showed reactivity of comparable intensity to complete rPhl p 6 and the two deletion variants (FIGS. 5A-C: lanes 15) whereas the rabbits preimmune serum showed no reactivity in the molecular weight range of the molecules (FIGS. 5A-C: lanes 16).

IgG1-Reactivity of Mouse Anti-rPhl p 6 or Anti-rPhl p 6 aa 31-110 Antisera to rPhl p 6

Figure 6:
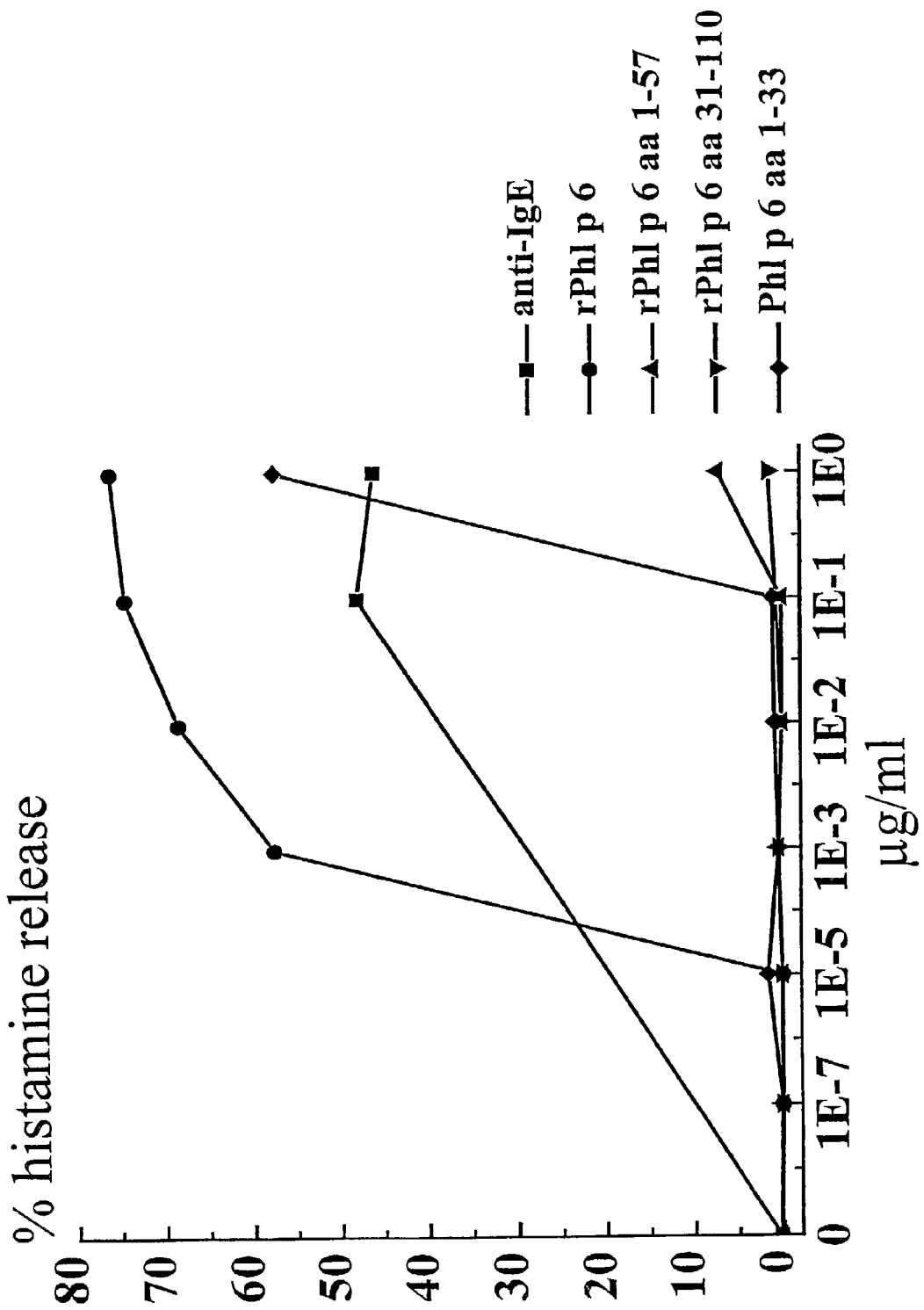
FIG. 6. Granulocytes from a patient allergic to grass pollen were incubated with various concentrations (1, $10^{-1}$, $10^{-2}$, $10^{-3}$, $10^{-5}$, and $10^{-7}$ μg/ml) of purified rPhl p 6 (points), rPhl p 6 aa 1-57 (up triangles), rPhl p 6 aa 31-110 (down triangles), rPhl p 6 aa 1-33 (rhombus) or an anti-IgE mAb (squares). Histamine released into the supernatant was measured by RIA and is displayed on the y-axis. Results represent the means of triplicate determinations.

Mouse IgG1 raised against complete rPhl p 6 and rPhl p 6 aa 31-110 react with rPhl p 6 (Table II).

rPhl p 6 Derivatives have a Greatly Reduced Capacity to Induce Histamine Release Granulocytes from a patient allergic to grass pollen were incubated with various concentrations of purified rPhl p 6, rPhl p 6 aa 1-57, rPhl p 6 aa 31-110, rPhl p 6 aa 1-33 or an anti-IgE mAb (E124.2.8 De2, Immunotech, Marseilles, France). Histamine released into the supernatant was measured by RIA (Inrmunotech)(FIG. 6). Purified rPhl p 6 induced a specific and dose-dependent histamine release from basophils of a patient allergic to grass pollen, whereas rPhl p 6-derivatives aa 1-57 and aa 31-110 did not induce any histamine release up to a concentration of 1 µg/ml. Phl p 6 aa 1-33 induced a 50% release of histamine at a concentration of 1 µg/ml, which represents an approximately 1000 fold reduction of histamine release compared to complete rPhl p 6.

Approximately 40% of allergic patients display immediate type symptoms after contact with grass pollen [Freidhoff et al., *Allergy Clin. Immunol.* 78:1190, 1986]. We have isolated cDNAs coding for isoforms and fragments of a major timothy grass pollen allergen, designated Phl p 6. Phl p 6 represents a 11.8 kDa protein allergen which is recognized by IgE antibodies of 75% of grass pollen allergic patients. The prevalence of IgE recognition of rPhl p 6 is thus in accordance with that reported earlier for natural Phl p 6 and indicates that carbohydrate moieties do not play a relevant role in IgE recognition of Phl p 6 [Lowenstein, H., *Allergy* 33:30 (1978); Matthiesen et al., *Phleum pratense*, pp. 189-191 (1993)]. In agreement with peptide sequence data obtained for natural Phl p 6 we found that the deduced amino acid sequence of rPhl p 6 shows a high degree of sequence homology with the N-terminal portions of group 5 grass pollen allergens, a family of 25-35 kDa major grass pollen allergens [Matthiesen et al., *Phleum pratense*, pp. 189-191, 1993; Vrtala, S. et al., *J. Immunol.* 151:4773, 1993]. Due to the presence of an N-terminal hydrophobic leader peptide, Phl p 6 represents an independent allergen, rather than a group 5 allergen fragment. In agreement with the proposal of other authors who analyzed a Phl p 6 encoding cDNA clone [Peterson et al., *Int. Arch. Allergy Immunol.* 108:55, 1995] we suggest that group 5 and group 6 allergens may have evolved from common ancestor genes similar as has been described for group 1 and group ⅔ grass pollen allergens [Dolecek et al., *FEBS Lett.* 335:299, 1993]. The assumption that Phl p 6 belongs to an independent group of grass pollen allergens is also supported by our finding that Phl p 6 shares few cross-reactive IgE epitopes with group 5 and no with other grass pollen allergens. The prediction of solvent accessibility indicated that many of the Phl p 6 N-terminal amino acids are solvent exposed while most of the C-terminal amino acid residues appeared to be buried. While no proof, this finding is in agreement with data obtained from the IgE epitope mapping experiments which indicate that the proteins N-terminus is critically involved in IgE recognition. It is however equally possible that the N-terminus itself represents a dominant IgE epitope or that deletion of the N-terminus affects conformational Phl p 6 IgE epitopes.

Expression of Phl p 6 in *E. coli* yielded large amounts of soluble and folded recombinant protein which contained almost exclusive alpha helical secondary structure. The alpha helical fold of Phl p 6 is a further confirmation that there are no common structural features which predispose a certain protein to behave as an allergen. While Phl p 6 is very likely an all alpha helical protein, Bet v 1, the major birch pollen allergen [Gajhede et al., *Nature Struct. Biol.* 3:1040, 1996] and Bet v 2, birch profilin [Fedorov et al., *Structure* 5:33, 1997] have a mixed alpha beta fold. As revealed by CD spectroscopical analysis, rPhl p 6 shares with other immunologically unrelated pollen allergens (e. g., Bet v 1 [Laffer et al., *J. Immunol.* 157:4943, 1996], Bet v 2 [Valenta et al., *Science* 253:557, 1991; Fedorov et al., *Structure* 5:33, 1997]) the remarkable intrinsic tendency to refold into a stable conformation after denaturation. Another feature that is shared by Phl p 6 and other important plant allergens is its high expression in pollen tissue. The fact that most of the plant allergens characterized so far are predominantly expressed in mature pollen may therefore be interpreted as a footprint of sensitization via the respiratory tract [Valenta et al., *J. Allergy Clin. Immunol.* 97:893, 1996].

By immunogold electron microscopy, Phl p 6 was primarily localized on the P-particles of mature pollen. P-particles are small polysaccharide-containing bodies which represent up to 30% of the contents of the dormant pollen grain and, during pollen germination transfer material into the growing pollen-tube wall [Heslop-Harrison et al., *Protoplasma* 112: 71, 1982; Heslop-Harrison et al., *Sex. Plant Reprod.* 10:65, 1997]. The occurence of Phl p 6 on the P-particles may be of clinical relevance as P-particles could act as small-sized (<2.5 micron) and therefore respirable allergen-carriers that bring Phl p 6 in immediate contact with the bronchial mucosa. A P-particle-linked intrusion of Phl p 6 into the deeper respiratory tract would thus explain the high prevalence (75%) of sensitization against this allergen although only a few grass species (*Phleum pratense, Poa pratensis*) contained rabbit anti-rPhl p 6-reactive moieties in the low (10-12 kDa) molecular weight range.

The *Escherichia coli*-expressed purified recombinant Phl p 6 allergen reacted with IgE antibodies of the majority of grass pollen allergic patients and induced basophil histamine release as well as immediate type skin reactions. It may therefore be used for in vitro as well as in vivo (skin test) diagnosis of grass pollen allergy. Our finding that deletion of the N-terminal portion of Phl p 6 dramatically reduced the allergens IgE binding capacity gave rise to the idea that it may be possible to construct Phl p 6 deletion variants which may be used for specific immunotherapy of grass pollen allergy with reduced anaphylactic side effects. A similar strategy was recently applied to disrupt the conformational IgE epitopes of the major birch pollen allergen Bet v 1 [Vrtala et al., *J. Clin. Invest.* 99:1673, 1997] but could not be predicted for Phl p 6 because the latter molecule contained continuous IgE epitopes. We produced N-terminally and C-terminally truncated versions of Phl p 6, of which the variant aa 31-110 and aa 1-57 showed almost completely abolished IgE binding capacity. We propose to use these two hypoallergenic Phl p 6 variants produced as recombinant molecules or by peptide chemistry as candidate vaccines against grass pollen allergy.

The invention claimed is:

1. A method for desensitization of a mammal suffering from IgE mediated allergy, said method comprising the step of administering to said mammal a therapeutically effective amount of an immunogenic and hypoallergenic composition which comprises a Phl p 6 molecule, wherein said Phl p 6 molecule is a polypeptide having an N-terminal truncation which makes the molecule at least lack IgE binding capacity, the Phl p 6 molecule being capable of raising an IgG immune response in the mammal and consisting of the amino acid sequence of SEQ ID NO: 18, SEQ ID NO: 19, or SEQ ID NO: 20, and a pharmaceutically acceptable carrier.

2. The method for desensitization of a mammal according to claim 1, wherein said polypeptide consists of the amino acid sequence of SEQ ID NO: 20.

3. A method for desensitization of a mammal suffering from IgE mediated allergy, said method comprising the step of administering to said mammal a therapeutically effective amount of an immunogenic and hypoallergenic composition which comprises a Phl p 6 molecule, wherein said Phl p 6 molecule is a polypeptide having a C-terminal truncation which makes the molecule at least lack IgE binding capacity, the Phl p 6 molecule being capable of raising an IgG immune response in the mammal and consisting of the amino acid sequence of SEQ ID NO: 22, and a pharmaceutically acceptable carrier.

4. A method for desensitization of a mammal suffering from IgE mediated allergy, said method comprising the steps of: administering to said mammal a therapeutically effective amount of an immunogenic and hypoallergenic composition which comprises (i) a Phl p 6 molecule having an N-terminal truncation which makes the molecule at least lack IgE binding capacity and consisting of the amino acid sequence of SEQ ID NO: 18, SEQ ID NO: 19, or SEQ ID NO: 20, and (ii) a Phl p 6 molecule having a C-terminal truncation which makes the molecule at least lack IgE binding capacity and consisting of the amino acid sequence of SEQ ID NO: 22, wherein the molecules of (i) and (ii) together span the complete sequence of Phl p 6.

5. The method for desensitization of a mammal according to claim 4, wherein said Phl p 6 molecule having an N-terminal truncation consists of the amino acid sequence of SEQ ID NO: 20.

6. The method according to claim 1, 3, or 4, wherein said IgE mediated allergy has the symptoms of allergic rhinitis, conjunctivitis, allergic asthma, or anaphylactic shock.

7. The method according to claim 1, 3, or 4, wherein said mammal is a human.

* * * * *

UNITED STATES PATENT AND TRADEMARK OFFICE
CERTIFICATE OF CORRECTION

PATENT NO. : 7,482,009 B2 Page 1 of 1
APPLICATION NO. : 10/142049
DATED : January 27, 2009
INVENTOR(S) : Rudolf Valenta et al.

It is certified that error appears in the above-identified patent and that said Letters Patent is hereby corrected as shown below:

Title Pg,

Item (75) Inventors, change "Stummfoll" to --Stumvoll--.

Item (75) Inventors, change "Padua" to --Padova--.

Signed and Sealed this

Twenty-fourth Day of March, 2009

JOHN DOLL
*Acting Director of the United States Patent and Trademark Office*